United States Patent [19]

Connolly et al.

[11] Patent Number: 5,315,012

[45] Date of Patent: May 24, 1994

[54] TETRAHYDROINDAZOLE, TETRAHYDROCYCLOPENTAPYRAZOLE, AND HEXAHYDROCYCLOHEPTAPYRAZOLE COMPOUNDS

[75] Inventors: Peter J. Connolly, Morristown; Michael P. Wachter, Bloomsbury, both of N.J.

[73] Assignee: Ortho Pharmaceutical Corporation, Raritan, N.J.

[21] Appl. No.: 98,536

[22] Filed: Sep. 9, 1993

Related U.S. Application Data

[62] Division of Ser. No. 886,569, May 20, 1992, Pat. No. 5,250,561, which is a division of Ser. No. 742,788, Aug. 8, 1991, Pat. No. 5,134,155.

[51] Int. Cl.$^5$ .................. C07D 231/54; C07D 231/56
[52] U.S. Cl. ............... 548/360.1; 548/359.1
[58] Field of Search .................. 548/359.1, 360.1

[56] References Cited

U.S. PATENT DOCUMENTS 4,851,425  11/1989  Smith ..................... 548/360.1

*Primary Examiner*—Robert W. Ramsuer
*Attorney, Agent, or Firm*—Ralph R. Palo

[57] ABSTRACT

Compounds of the general formula I:

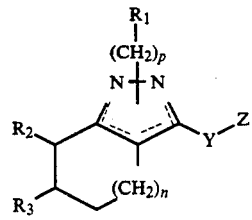

are disclosed as useful in the treatment or prevention of hypercholesterolemia, hyperlipoproteinemia and atherosclerosis. Novel intermediate compounds used to make the compound of formula I are also disclosed.

1 Claim, No Drawings

TETRAHYDROINDAZOLE, TETRAHYDROCYCLOPENTAPYRAZOLE, AND HEXAHYDROCYCLOHEPTAPYRAZOLE COMPOUNDS

This is a division, of application Ser. No. 886,569, filed May 20, 1992 now U.S. Pat. No. 5,250,561, which is hereby incorporated by reference, which is a divisional of Ser. No. 742,788, filed Aug. 8, 1991, now U.S. Pat. No. 5,134,155.

BACKGROUND OF THE INVENTION

Compounds which inhibit HMG-CoA reductase, the enzyme controlling the rate-limiting step in cholesterol biosynthesis, are assuming an important role in the management of certain forms of hyperlipidemia. Lovastatin, disclosed in U.S. Pat. No. 4,231,938, has been approved for use in the treatment of primary hypercholesterolemia, a disease characterized by normal serum triglyceride levels and elevated serum levels of low density lipoprotein (LDL) cholesterol and total cholesterol. In several large clinical studies, lovastatin was found to decrease plasma LDL and total cholesterol concentrations 25% to 40% while causing small but significant increases (up to 10%) in high density lipoprotein (HDL) cholesterol concentration. When compared with cholestyramine and probucol, two drugs used in the treatment of primary hypercholesterolemia, lovastatin reduced LDL cholesterol levels to a significantly greater extent. In addition, combined administration of lovastatin with other hypolipidemic agents was found to potentiate their effects on LDL and total cholesterol concentrations.

The biochemical target for lovastatin is HMG-CoA reductase, the enzyme which catalyzes the reduction of HMG-CoA to mevalonic acid. Lovastatin, in its open dihydroxy acid form, is a reversible, competitive inhibitor of the enzyme. A number of compounds structurally related to lovastatin have been shown to be inhibitors of HMG-CoA reductase. These include simvastatin (U.S. Pat. No. 4,444,784 and related compounds disclosed in U.S. Pat. No. 4,444,784). Sankyo has reported a related compound, pravastatin (U.S. Pat. No. 4,346,227). Sandoz has reported a number of HMG-CoA reductase inhibitors: indoles (U.S. Pat. No. 4,739,073), pyrazoles (U.S. Pat. No. 4,613,610), imidazoles (U.S. Pat. No. 4,808,607), and pyrazolopyridines (U.S. Pat. No. 4,822,799). Merck disclosed biphenyl-containing inhibitors in U.S. Pat. No. 4,375,475. Hoechst AG disclosed non-heterocyclic HMG-CoA reductase inhibitors in *Tetrahedron Letters*, 1988, 29, 929. Bristol-Myers reported tetrazole-containing compounds in UK Patent 2,202,846. Acylpyrroles are reported in U.S. Pat. No. 4,681,893 by Warner-Lambert. Warner-Lambert also disclosed pyrimidines in U.S. Pat. No. 4,868,185 and quinolines in U.S. Pat. No. 4,761,419. Bayer AG reported tri-arylpyrroles in European Patent 287,890. Rorer reported aryl-cycloalkene and aryl-cycloalkadiene inhibitors in U.S. Pat. Nos. 4,892,884 and 4,900,754. Squibb reported a number of potent compounds based on a variety of heterocycles in *Journal of Medicinal Chemistry*, 1990, 33, 2852. Finally, Upjohn disclosed in WO 867,357 an anti-inflammatory, anti-allergic compound generically described as cyclopentapyrazole.

The compounds of the present invention are structurally different from the known compounds and have been shown to be potent inhibitors of HMG-CoA reductase and cholesterol biosynthesis.

SUMMARY OF THE INVENTION

Novel tetrahydroindazole, tetrahydrocyclopentapyrazole, and hexahydrocycloheptapyrazole compounds of the general formula I:

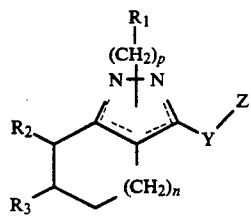

wherein $R_1$, $R_2$, $R_3$, Y, Z, n, and p are defined hereinafter have been found to be potent compounds for inhibiting HMG-CoA reductase and cholesterol biosynthesis and are thus useful in the treatment or prevention of hypercholesterolemia, hyperlipoproteinemia, and atherosclerosis.

DETAILED DESCRIPTION OF THE INVENTION

The present invention is directed to compounds of the following general formula I:

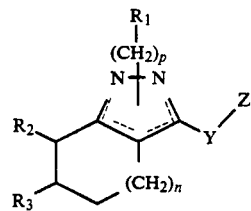

$R_1$ is selected from any one of H, $C_1$–$C_8$ alkyl, aryl, or substituted aryl. The $R_1$ substituent may be attached either directly or indirectly to either of the ring nitrogens but not both at the same time. Two double bonds represented by the dotted line in the nitrogen containing ring are positioned accordingly depending upon the position of the $R_1$ substituent. Examples of suitable $R_1$ substituents include 4-fluorophenyl and 4-chlorophenyl.

$R_2$ is selected from any one of H, $C_1$–$C_8$ alkyl, aryl, substituted aryl, aralkyl wherein the alkyl portion is $C_1$–$C_4$, substituted aralkyl wherein the alkyl portion is $C_1$–$C_4$, aralkenyl wherein the alkenyl portion is $C_1$–$C_4$, or $C_3$–$C_8$ cycloalkyl such as cyclopropyl, cyclobutyl, cyclopentyl and the like. Examples of suitable $R_2$ groups include H, 4-fluorobenzyl, 3-phenyl-2-propenyl, cyclohexyl, ethyl, methyl, 1-naphthylmethyl, 2-naphthylmethyl, 4-phenylbenzyl, benzyl, 4-chlorobenzyl, 4-isopropylbenzyl, 4-methoxybenzyl and 4-t-butylbenzyl.

$R_3$ is H.

$R_2$ and $R_3$ may be taken together to form a benzo or naphtho ring system.

Y is $C_1$–$C_8$ alkyl or $C_1$–$C_8$ alkenyl such as CH=CH and CH=C(CH$_3$).

Z is selected from any one of:

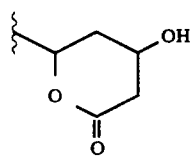

II

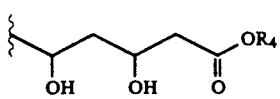

III wherein $R_4$ is H, $C_1$–$C_8$ alkyl, a protonated amine of the formula $HN(R_5)_3{}^+$ wherein $R_5$ is H or $C_1$–$C_8$ alkyl, or a cation such as $Na^+$, $K^+$, $Li^+$, $Ca^{2+}$, or $Mg^{2+}$.

The values for n are 0 to 3 and the values for p are 0 to 3.

The compounds of formula I can be generally represented by three sub-groups of compounds represented by formulas I(a), I(b), and I(c) which are set forth as follows:

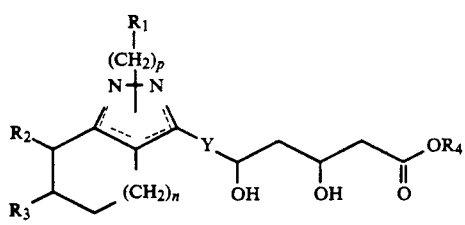

I(a)

wherein $R_4$ is any of $C_1$–$C_8$ alkyl, and $R_1$, $R_2$, $R_3$, Y, n, and p are as defined above; or

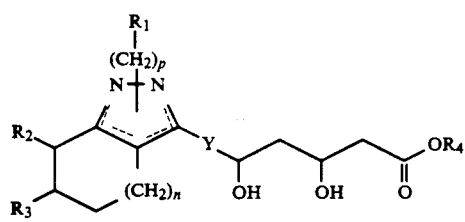

I(b)

wherein $R_4$ is H, a cation such as $Na^+$, $K^+$, $Li^+$, or a protonated amine of the formula $HN(R_5)_3+$, wherein $R_5$ is H or $C_1$–$C_8$ alkyl, and $R_1$, $R_2$, $R_3$, Y, n, and p are as defined above; or

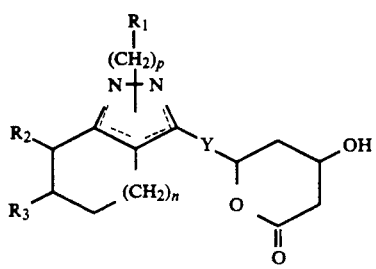

I(c)

wherein $R_1$, $R_2$, $R_3$, Y, n, and p are as defined above.

Also within the scope of this invention are intermediate compounds which are useful in making the compounds of formula I. The intermediate compounds are represented by the general formula X:

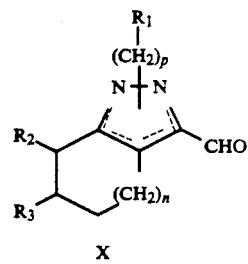

X wherein
$R_1$, n, and p are as defined above.

$R_2$ is selected from any one of H, $C_1$–$C_8$ alkyl, aryl, substituted aryl, aralkyl wherein the alkyl portion is $C_1$–$C_4$, substituted aralkyl wherein the alkyl portion is $C_1$–$C_4$, aralkenyl wherein the alkenyl portion is $C_1$–$C_4$, or $C_3$–$C_8$ cycloalkyl such as cyclopropyl, cyclobutyl, cyclopentyl and the like.

$R_3$ is H.

$R_2$ and $R_3$ may be taken together to form a benzo or naphtho ring system.

The term "aryl," as used herein alone or in combination with other terms, indicates aromatic hydrocarbon groups such as a phenyl or naphthyl group. The term "aralkyl" indicates a radical containing a lower $C_1$–$C_8$ alkyl group substituted with an aryl radical or substituted aryl radical as defined above.

The aryl groups and the ring formed by $R_2$ and $R_3$ may be independently substituted with any of $C_1$–$C_8$ alkyl, such as methyl, ethyl, propyl, isopropyl, t-butyl, and sec-butyl; alkoxy such as methoxy and t-butoxy; halo such as fluoro, chloro, bromo, and iodo; or nitro.

As used herein alkyl and alkoxy include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 3-methylpentyl. Alkoxy radicals are oxygen ethers formed from the previously described straight or branched chain alkyl groups. The term "independently" is used with respect to aryl and ring substituents to indicate that when more than one of such substituents is possible such substituents may be the same or different from each other. Position 1 in the N-containing ring is the N atom adjacent to the ring fusion.

The compounds produced according to the invention include the various individual isomers as well as the racemates thereof, e.g. the isomers arising from the various attachments on the side chain Z as well as the substituents $R_2$ and $R_3$.

The compounds of formula I and intermediates of formula X may be prepared according to the following general reaction scheme, which as is apparent contains a plurality of alternative routes depending upon starting materials and the reactions carried out.

Reaction Scheme
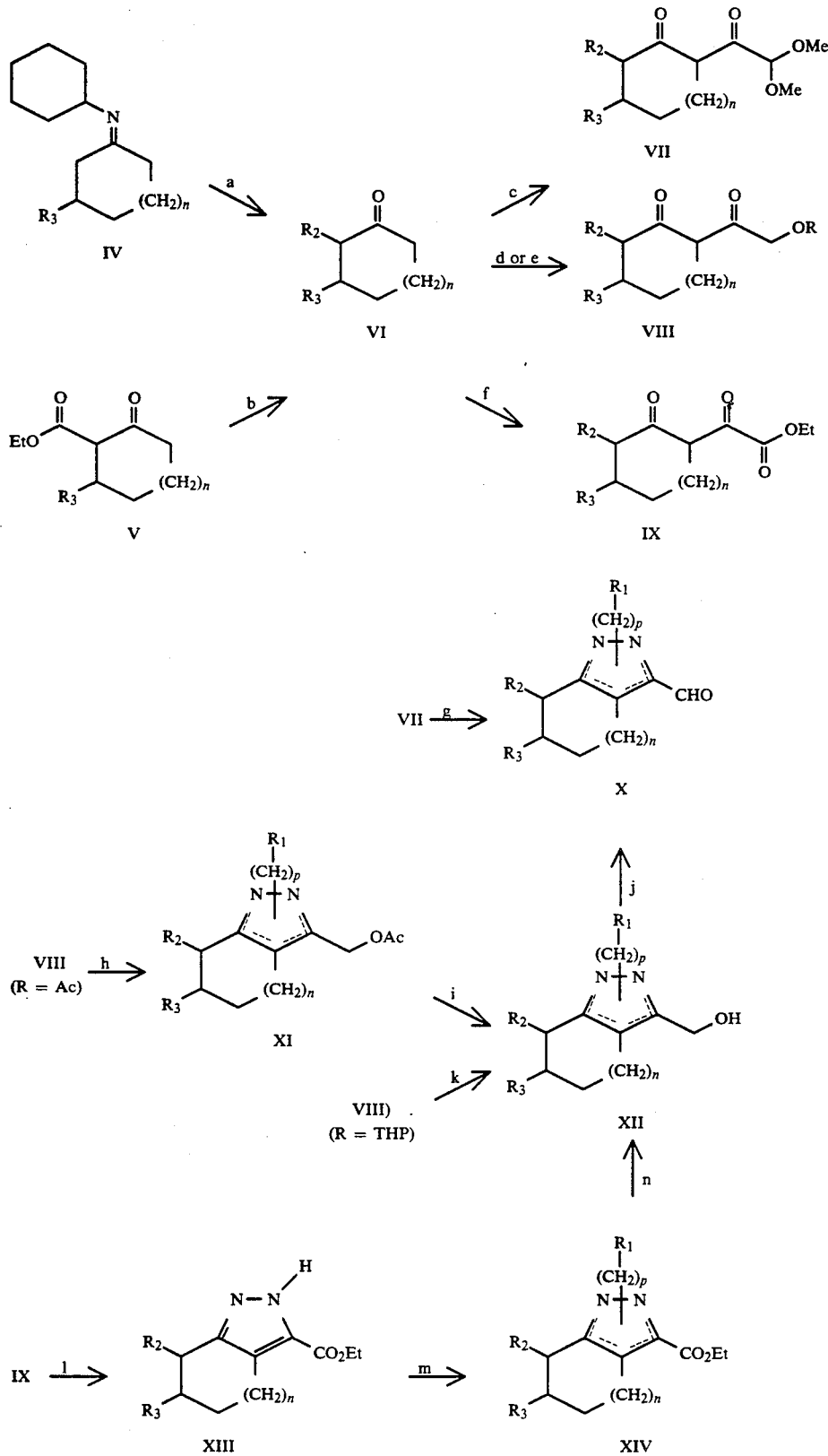

-continued
Reaction Scheme

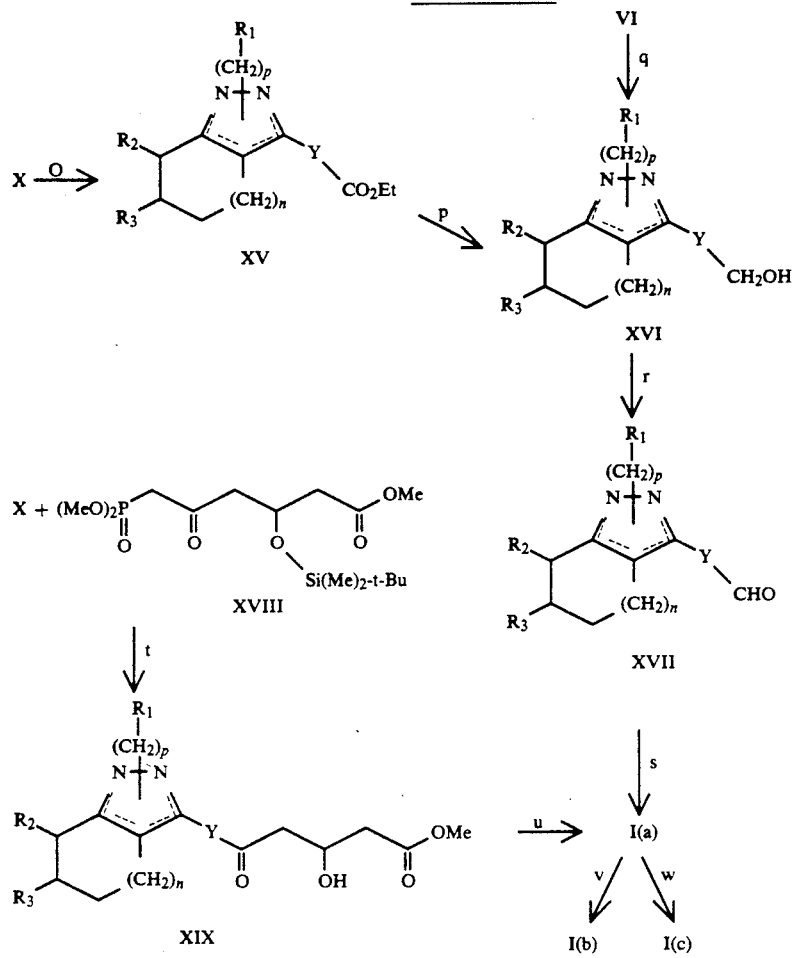

If desired, the substituted cyclic ketone VI may be obtained from commercial suppliers (Aldrich Chemical Co., Lancaster Synthesis Ltd., or Wiley Organics). Alternatively, compound VI may be prepared as shown in the reaction scheme by treatment of imine IV (Stork, G., Dowd, S. R. *J. Am. Chem. Soc.*, 1963, 85, 2178–80) in an inert solvent such as THF with an appropriate base such as s-BuLi or LiN(i-Pr)$_2$ (LDA) at −78° to 0° C. for 15 to 45 min under N$_2$, followed by alkylation at 0° C. to RT (room temperature) for 16 h, followed by hydrolysis of the resulting imine with 2N HCl at RT for 5 h. Alternatively, compound VI may be prepared by treatment of the 2-carboethoxy cyclic ketone V (commercially available from Aldrich Chemical Co.) in an inert solvent such as benzene or DMF with an appropriate base such as NaH at 0° to 25° C. for 30 to 60 min under N$_2$, followed by alkylation at 0° C. to RT for 2 to 3 days, followed by hydrolysis of the ester and decarboxylation of the resulting acid with 6N HCl at reflux for 2 to 3 days.

Compound VI can be treated with an appropriate base, such as LDA or LiN(SiMe$_3$)$_2$, in an inert solvent, such as THF, at −78° C. to 0° C. and acylated with methyl dimethoxyacetate at 0° C. to RT for 16 h to give the diketone VII. Compound VII is dissolved in an appropriate solvent, such as EtOH, and treated with a substituted hydrazine for 16 h at RT. The resulting acetal is hydrolyzed with 1N HCl at reflux to give the aldehyde X as a separable mixture of regioisomers.

Compound X can also be prepared from compound VI by several alternate routes. Thus, compound VI is treated with pyrrolidine and acetoxyacetyl chloride to give the acetoxy methyl diketone VIII (R=Ac: Dolmazon, R. *J. Heterocyclic Chem.*, 1982, 19, 117–121). Reaction of VIII with a substituted hydrazine in a suitable solvent, such as EtOH, from RT to reflux for 4 to 10 h gives the regioisomeric mixture of acetoxy compounds XI, which is dissolved in an alcoholic solvent such as MeOH and hydrolyzed with 1N NaOH at RT to provide the separable mixture of alcohols XII. Alternatively, the THP derivative of compound VIII (R=THP), prepared by the treatment of compound VI and ethyl (tetrahydropyranyloxy)acetate (Ireland, R. *Tetrahedron Lett.*, 1989, 30, 919–922) in ether with a suitable base, such as NaH or NaOEt, from 0° C. to RT for 16 h, can be treated with a substituted hydrazine at reflux for 4 h, followed by hydrolysis of the THP group with 1N HCl to give the separable mixture of alcohols XII.

Alternatively, compound VI is treated with NaH and diethyl oxalate to give the 2-substituted dioxoacetate IX (Tsuboi, S. *J. Org. Chem*, 1987, 52, 1359–62). Treatment of compound IX in MeOH with hydrazine hydrate at RT to 60° C. for 16 h gives the 3-carboethoxy compound XIII. The separable regioisomeric mixture of esters XIV is prepared by treating compound XIII with a suitable base, such as NaH, in an inert solvent, such as DMF, at 140° C. for 15 min under N$_2$, followed by the addition of the alkylating agent at 140° C. The alcohol XII is prepared by reduction of the corresponding 3-carboxylate XIV with a suitable reducing agent, such as LiAlH$_4$, in an inert solvent, such as THF, at 0° C. to RT for 2 to 3 h under N$_2$. Oxidation of compound XII with either MnO$_2$ in an appropriate solvent, such as benzene, or pyridinium chlorochromate in an appropriate solvent, such as methylene chloride, gives the corresponding aldehyde X.

Treatment of compound X with NaH and triethyl phosphonoacetate or triethyl phosphonopropionate in an inert solvent such as THF at 0° to RT for 16 h gives the corresponding ester XV. Reduction of the ester is accomplished by treatment of XV with (i-Bu)$_2$AlH in an inert solvent, such as toluene or THF, for 1 to 2 h at 0° C. under N$_2$ to give the alcohol XVI. Alternatively, compound XVI can be prepared from the appropriately substituted cyclic ketone VI by treatment of said ketone with a substituted hydrazine and an appropriate base, such as NaOAc, in EtOH at reflux for 3 h to give the hydrazone. The hydrazone is then treated with a suitable base, such as LDA, at −10° C. and acylated with methyl 4-tetrahydropyranyloxy-2-butenoate (Harnish, W.; Morera, E.; Ortar. G. *J. Org. Chem.*, 1985, 50, 1990–2); the resulting intermediate is treated with 3N HCl at reflux for 15 min, followed by reaction with pyridinium p-toluenesulfonate at reflux for 8 h under N$_2$ to give the substituted alcohol XVI. Oxidation of alcohol XVI by treatment with MnO$_2$ in an appropriate solvent, such as benzene, at reflux for 3 h or with CrO$_3$ and pyridine in an appropriate solvent, such as methylene chloride, gives aldehyde XVII. Ethyl acetoacetate is treated with an appropriate base, such as LDA, or mixture of bases, such as NaH and nBuLi, and reacted with compound XVII at 0° to −10° C. for 1 to 2 h in an inert solvent such as THF. Reaction of the intermediate ester with Et$_3$B in a solvent mixture such as 1:4 MeOH:THF at 0° C., followed by treatment with NaBH$_4$ at −78° C. to RT for 16 h, gives the dihydroxyheptenoate I(a).

Alternatively, compound I(a) can be prepared by the reaction of compound X with methyl 3-[(t-butyldimethylsilyl)oxy-6-(dimethoxyphosphinyl)-5-oxohexanoate XVIII (Theisen, P. D.; Heathcock, C. H. *J. Org. Chem.*, 1988, 53, 2374–81), LiCl, and DBU in an appropriate solvent, such as acetonitrile, at RT under N$_2$ for 6 h to give 3-hydroxy-5-oxoheptenoate XIX. Treatment of ester XIX with Et$_3$B in a solvent mixture such as 1:4 MeOH:THF at 0° to −78° C., followed by reaction with NaBH$_4$ at −78° C. to RT for 16 h gives the dihydroxyheptenoate I(a). Compound I(a) can be hydrolyzed with aqueous NaOH or KOH and a suitable alcoholic solvent, followed optionally by neutralization with dilute aqueous HCl and treatment with an amine base, to give the dihydroxyheptenoic acid derivative I(b). Hydrolysis of compound I(a) as described above to the crude acid, followed by treatment of said acid with an appropriate carbodiimide, such as 1-cyclohexyl-3-(2-morpholinoethyl) carbodiimide metho-p-toluenesulfonate, in an inert solvent, such as methylene chloride, at 0° C. to RT for 16 h, gives the tetrahydropyranyl compound I(c).

The compounds of this invention are useful as hypocholesterolimic or hypolipidemic agents by virtue of their ability to inhibit the biosynthesis of cholesterol through the inhibition of the enzyme 3-hydroxy-3-methylglutaryl coenzyme A reductase (HMG-CoA reductase). The ability of the compounds of the present invention to inhibit the biosynthesis of cholesterol was measured by two different tests.

HMG-CoA Reductase Isolation And Assay

Livers were harvested from male Wistar rats (250 g) following a five day feeding with powdered chow containing 2% cholestyramine. Ammonium sulfate precipitated HMG-CoA reductase was prepared from these livers according to the method of Heller, et. al. (Heller, R. A., Shrewsbury, M. A. *Journal of Biological Chemistry*, 251, 1976, 3815–3822). HMG-CoA reductase activity was measured using a modification of the procedure of Edwards, et. al. (Edwards, P. A., Lemongello, D., Fogelman A. M. *Journal of Lipid Research*, 20, 1979, 40–46). The effects of compounds on HMG-CoA reductase activity were determined by combining the compound with the enzyme and preincubating for 10 minutes prior to addition of the substrate HMG-CoA reductase.

Cell Culture Cholesterol Biosynthesis Assay

Hep-G2 cells obtained from the American Type Culture Collection were maintained in MEM (minimal essential medium) obtained from GIBCO containing Earles salts and supplemented with 10% HI-FBS. For cholesterol biosynthesis experiments, cells were plated into T25 flasks. When the cells were ⅔ confluent, they were fed MEM containing Earles salts and delipidated serum protein (DLP) at 5 mg/mL and then incubated for a period of 24 h. DLP was prepared according to the procedure of Rothblat, et. al. (Rothblat, G. H., Arrbogast, L. Y., Ouellette, L., Howard, B. V. *In Vitro (Rockville)*, 12, 1976, 554–557). The DLP medium was then removed and 3.3 mL of media containing the drug indicated was added. Monolayers were incubated with drug for 2.5 h at which time $^{14}$C-acetate (0.2 mCi/12 mmol) was added and cells incubated for an additional 3 h. The reaction was stopped by the addition of 0.2 mL of 12N H$_2$SO$_4$; $^3$H-cholesterol and $^3$H-oleic acid were added as internal recovery standards, and samples were saponified. Fatty acids were extracted and digitonin precipitable sterols were recovered according the procedure of Kanduch and Saucier (Kandutch. A. A., Saucier, S. E. *Journal of Biological Chemistry*, 244, 1969, 2299–2305). To adjust for cell number per flask, the cholesterol synthesized was normalized to the fatty acids synthesized and results were expressed as percent inhibition vs. control.

The activities of certain representative examples are shown in Tables I–V. In the Tables, Me means methyl, Et is ethyl, Pr is propyl, Bu is butyl, c-Hex is cyclohexyl, Ph is phenyl, Nap is naphthyl, MeO is methoxy, and Biphenyl is (1,1'-biphenyl)-4-yl. Each of the compounds was tested in the form of a racemic mixture.

Each of the compounds in Tables I–V was tested in one or both of the biological assays. The symbol "nt" indicates that a particular compound was not tested.

TABLE I

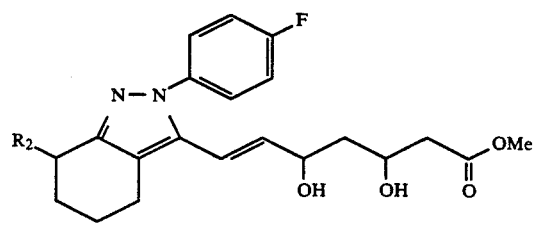

Compound             Cell Culture Cholesterol

TABLE I-continued

| Number | R₂ | Biosynthesis IC$_{50}$ (μM) |
|---|---|---|
| 42 | (2-Nap)—CH$_2$ | 0.365 |
| 43 | (4-i-Pr—Ph)—CH$_2$ | 0.12 |

TABLE II

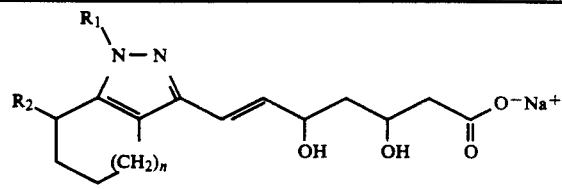

| Compound Number | n | R$_1$ | R$_2$ | HMG-CoA Reductase IC$_{50}$ (nM) | Cell Culture Cholesterol Biosynthesis IC$_{50}$ (μM) |
|---|---|---|---|---|---|
| 2 | 0 | 4-F—Ph | H | 100,000 | nt |
| 3 | 1 | 4-F—Ph | (4-F—Ph)—CH$_2$ | 31,000 | 27 |
| 4 | 1 | 4-F—Ph | c-Hex | 47,000 | nt |
| 5 | 1 | 4-F—Ph | Et | 35,000 | nt |
| 6 | 1 | 4-F—Ph | Me | 100,000 | nt |
| 7 | 1 | 4-F—Ph | Ph—(CH$_2$)$_2$ | nt | >10 |
| 8 | 1 | 4-F—Ph | Ph—CH=CH—CH$_2$ | 3,000 | nt |
| 9 | 2 | (4-F—Ph)—CH$_2$ | H | 100,000 | nt |

TABLE III

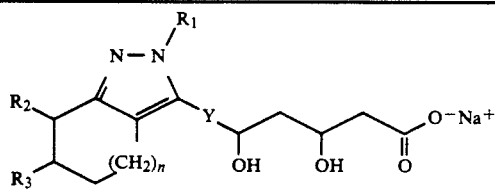

| Compound Number | n | R$_1$ | R$_2$ | R$_3$ | Y | HMG-CoA Reductase IC$_{50}$ (nM) | Cell Culture Cholesterol Biosynthesis IC$_{50}$ (μM) |
|---|---|---|---|---|---|---|---|
| 1 | 1 | 4-F—Ph | (Biphenyl)-CH$_2$ | H | CH=CH | 2.7 | 0.24 |
| 10 | 0 | 4-F—Ph | H | H | CH=CH | 5,100 | nt |
| 11 | 1 | 4-F—Ph | (1-Nap)—CH$_2$ | H | CH=CH | 26 | 0.37 |
| 12 | 1 | 4-F—Ph | (2-Cl—Ph)—CH$_2$ | H | CH=CH | 100 | 1.3 |
| 13 | 1 | 4-F—Ph | (2-Nap)—CH$_2$ | H | CH=CH | 5.6 | 0.33 |
| 14 | 1 | 4-F—Ph | (3-MeO—Ph)—CH$_2$ | H | CH=CH | 48 | 1.09 |
| 15 | 1 | 4-F—Ph | (3,4-di-MeO—Ph)—CH$_2$ | H | CH=CH | 168 | 3.9 |
| 16 | 1 | 4-F—Ph | (4-Cl—Ph)—CH$_2$ | H | CH=CH | 58 | 0.36 |
| 17 | 1 | 4-F—Ph | (4-F—Ph)—CH$_2$ | H | CH=CH | 150 | 0.70 |
| 18 | 1 | 4-F—Ph | (4-i-Pr—Ph)—CH$_2$ | H | CH=CH | 14 | 0.26 |
| 19 | 1 | 4-F—Ph | (4-Me—Ph)—CH$_2$ | H | CH=CH | 19 | 0.13 |
| 20 | 1 | 4-F—Ph | (4-MeO—Ph)—CH$_2$ | H | CH=CH | 14 | 0.46 |
| 21 | 1 | 4-F—Ph | (4-t-Bu—Ph)—CH$_2$ | H | CH=CH | 16 | 0.135 |
| 22 | 1 | 4-F—Ph | 6,7-Benzo | | CH=CH | 13,000 | nt |
| 23 | 1 | 4-F—Ph | c-Hex | H | CH=CH | 7,700 | nt |
| 24 | 1 | 4-F—Ph | Et | H | CH=CH | 1,000 | nt |
| 25 | 1 | 4-F—Ph | H | H | CH=CH | 2,500 | nt |
| 26 | 1 | 4-Cl—Ph | H | H | CH=CH | 8,800 | nt |
| 27 | 1 | 4-F—Ph | H | H | CH=C(Me) | 2,700 | nt |
| 28 | 1 | 4-F—Ph | Me | H | CH=CH | 1,100 | nt |
| 29 | 1 | 4-F—Ph | n-Pr | H | CH=CH | 1,300 | nt |
| 30 | 1 | 4-F—Ph | Ph | H | CH=CH | 3,100 | nt |
| 31 | 1 | 4-F—Ph | Ph—CH$_2$ | H | CH=CH | 85 | 0.22 |

TABLE III-continued

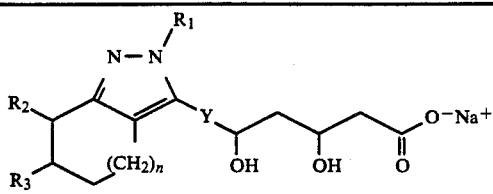

| Compound Number | n | $R_1$ | $R_2$ | $R_3$ | Y | HMG-CoA Reductase $IC_{50}$ (nM) | Cell Culture Cholesterol Biosynthesis $IC_{50}$ ($\mu$M) |
|---|---|---|---|---|---|---|---|
| 32 | 1 | 4-F—Ph | Ph—$(CH_2)_2$ | H | CH=CH | 334 | 1.75 |
| 33 | 1 | 4-F—Ph | Ph—$(CH_2)_3$ | H | CH=CH | 160 | 1.1 |
| 34 | 1 | 4-F—Ph | Ph—CH=CH—$CH_2$ | H | CH=CH | 32 | 1.3 |
| 35 | 1 | 4-F—Ph | s-Bu | H | CH=CH | 1,000 | nt |
| 36 | 2 | 4-F—Ph | 7,8-Benzo | | CH=CH | 2,100 | nt |
| 37 | 2 | 4-F—Ph | H | H | CH=CH | 3,800 | nt |
| 38 | 2 | (4-F—Ph)—$CH_2$ | H | H | CH=CH | 23,000 | nt |

TABLE IV

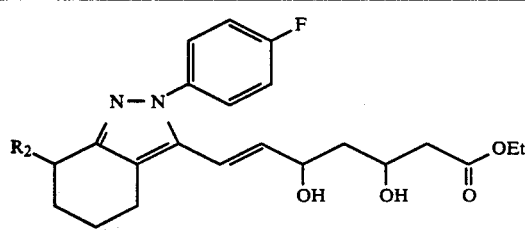

| Compound Number | $R_2$ | HMG-CoA Reductase $IC_{50}$ (nM) | Cell Culture Cholesterol Biosynthesis $IC_{50}$ ($\mu$M) |
|---|---|---|---|
| 47 | Ph—$CH_2$ | 120 | 0.29 |
| 58 | (3-MeO—Ph)—$CH_2$ | 210 | 0.80 |
| 60 | (4-Cl—Ph)—$CH_2$ | nt | 0.46 |
| 62 | (4-Me—Ph)—$CH_2$ | 70 | 0.20 |
| 64 | (4-t-Bu—Ph)—$CH_2$ | 30 | nt |

TABLE V

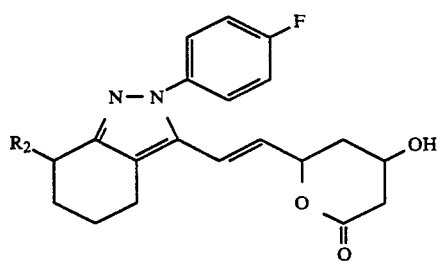

| Compound Number | $R_2$ | HMG-CoA Reductase $IC_{50}$ (nM) | Cell Culture Cholesterol Biosynthesis $IC_{50}$ ($\mu$M) |
|---|---|---|---|
| 79 | Ph—$CH_2$ | 750 | 0.26 |
| 80 | (2-Et)Bu | 29,000 | nt |
| 81 | (2-Nap)—$CH_2$ | nt | 0.39 |
| 82 | (4-t-Bu—Ph)—$CH_2$ | 70 | 0.23 |
| 83 | H | 9,000 | nt |

The pharmaceutical compositions containing compounds of the present invention are comprised of the compounds of the present invention and a pharmaceutically acceptable carrier in either solid or liquid form. Solid form preparations include powders, tablets, dispersible granules, capsules, etc. The carrier may also be one or more substances which act as diluents, flavoring agents, solublizers, lubricants, suspending agents, binders, or tablet disintegrating agents and they may also be encapsulating materials. Suitable carriers are magnesium carbonate, magnesium stearate, talc, lactose, sugar, peptin, dextrin, starch, methyl cellulose, sodium carboxyl methyl cellulose, and the like. Liquid form preparations include solutions which are suitable for oral or parenteral administration, or suspensions and emulsions suitable for oral administration. Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Aqueous solutions for oral administration can be prepared by dissolving the active compound in water and adding suitable flavorants, coloring agents, stabilizers and thickening agents as required. Aqueous suspensions for oral use can be made by dispersing the finely divided active component in water together with a viscous material such as a natural or synthetic gum, resin methyl cellulose, sodium carboxy methyl cellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used in the specification and claims herein refers to physically discrete units suitable as unit dosages, each unit containing a predetermined quantity of active ingredient calculated to produce the desired therapeutic effect in association with the required pharmaceutical carrier.

In therapeutic use as hypolipidemic or hypochloesterolemic agents, the compounds utilized in the pharmaceutical method of this invention are administered to the patient at dosage levels of from about 0.01–100 mg/kg per day. The dosages, however, may be varied depending upon the requirements of the patient, the severity of the condition being treated, and the compound being employed. Determination of optimum dosages for a particular situation is within the skill of the art.

In the following examples, Examples 13, 14, 20 and 21, Tables 8, 9A, 9B, 13A, 13B, and 14, illustrate the preparation of the final compounds I(a-c) according to the present invention. Examples 3 and 11, Tables 3A, 3B, and 6, illustrate the preparation of the novel intermediate of the compound of formula X. The remainder of the examples illustrate the preparations of the various intermediates according to the reaction scheme set forth previously that are made to produce the compounds of the present invention. For ease of reference, each example is keyed to a particular step in the reaction scheme. Moreover, there are specific examples of one compound for each step in the sequence and a general procedure for making the other compounds which are listed in the table at the end of each example.

Unless otherwise noted, materials used in the examples were obtained from commercial suppliers and were used without further purification. Tetrahydrofuran (THF) was distilled from Na/benzophenone immediately prior to use. The following chemicals were obtained from Sigma Chemical Co: digitonin, 3-hydroxy-3-methylglutaryl coenzyme A (HMG-CoA), and $\beta$-nicotinamide adenine dinucleotide phosphate, reduced form (NADPH). The (1-$^{14}$C)-acetate was obtained from both Research Biochemicals, Inc. (RBI) and New England Nuclear-Dupont (NEN). The (3-$^{14}$C)-HMG-CoA was obtained from NEN, and (7-$^3$H)-cholesterol and (7-$^3$H)-cholesteryl oleate were obtained from Amersham. HI-FBS (heat-inactivated fetal bovine serum) and calf serum were obtained from Grand Island Biological Co. (GIBCO). Lovastatin was obtained from Merck. Lovastatin-Na was prepared from Lovastatin by reaction with sodium hydroxide. Pravastatin was obtained from Sigma, and XU-62320 was obtained from Sandoz. Diisopropylamine was distilled from $CaH_2$ and was stored over 4A molecular sieves. 1,8-Diazabicyclo[5.4.0]undec-7-ene (DBU) was used without purification. Dimethylformamide (DMF) was dried over 4A sieves prior to use. Melting points were determined on a Thomas-Hoover apparatus and are uncorrected. Nuclear magnetic resonance (NMR) spectra were measured in the indicated solvent with tetramethylsilane (TMS) as the internal standard using the following spectrometers: Bruker WP-100SY (100 MHz $^1$H, 25 MHz $^{13}$C), General Electric QE-300 (300 MHz $^1$H, 75 MHz $^{13}$C), Varian XL-400 (400 MHz $^1$H, 100 MHz $^{13}$C). NMR chemical shifts are expressed in parts per million (ppm) downfield from internal TMS using the $\delta$ scale. $^1$H Hertz). $^{13}$C NMR data are reported for proton-decoupled spectra and are tabulated in order. Infrared (IR) spectra were determined on a Nicolet 5DXB FT-IR spectrophotometer. Chemical ionization (DCI), electron impact (EI), and fast atom bombardment (FAB) mass spectra (MS) were determined on a Finnegan MAT 8230 spectrometer. Elemental analyses were carried out on a Perkin Elmer 240C analyzer. Analytical thin layer chromatography (TLC) was done with Merck Silica Gel 60 $F_{254}$ plates (250 micron). Flash chromatography and medium pressure liquid chromatography (MPLC) were done with Merck Silica Gel 60 (230-400 mesh).

EXAMPLE 1

2-[(1,1'-Biphenyl)-4-ylmethyl]cyclohexanone (Compound(hereinafter CP) 84, Reaction Scheme(hereinafter RS)Step a)

A 1.3M solution of s-BuLi in hexanes (51.8 mmol, 39.8 mL) was added over a 15 min period to a $-78°$ C. solution containing 9.29 g (51.8 mmol) of N-cyclohexylidine cyclohexylamine (Stork, G., Dowd, S. R. *J. Am. Chem. Soc.*, 1963, 85, 2178-80) in 75 mL of THF under $N_2$. After 30 min, the cooling bath was removed and the cloudy solution was allowed to warm to $0°$ C. A solution of 10.0 g (49.3 mmol) of 4-(chloromethyl)biphenyl in 30 mL of THF was added and the resulting mixture was stirred at room temperature overnight. A 40 mL portion of 2N aqueous HCl was added and the mixture was stirred for 5 h. $Et_2O$ (200 mL) was added and the organic solution was washed successively with water, saturated $NaHCO_3$, and brine. The organic layer was dried over $Na_2SO_4$ and concentrated to give 13.1 g of an off-white solid. Recrystallization from EtOAc:hexanes afforded 9.22 g (71%) of the title compound as a white solid, m.p. 78°-79° C.; $^1$H NMR (CDCl$_3$, 300 MHz) 1.40 (m, 1), 1.65 (m, 2), 1.83 (m, 1), 2.10 (m, 2), 2.35 (m, 1), 2.52 (m, 2), 2.60 (m, 1), 3.27 (dd, 1, J=5, 13.5 Hz), 7.2-7.6 (complex); IR (KBr) 1695 cm$^{-1}$; MS (DCI) m/z 265 (base). Anal. Calcd. for $C_{19}H_{20}O$: C, 86.32; H, 7.63. Found: C, 86.66; H, 7.98.

General procedure for the preparation of 2-substituted cyclohexanones shown in Table 1:

Method A (RS step a): s-BuLi (50 mmol) was added under $N_2$ to a solution of 50 mmol of the cyclohexylimine of N-cyclohexylidine cyclohexylamine in 75 mL of THF at $-78°$ C. The resulting cloudy solution was stirred for 30 min and was allowed to warm to $0°$ C. A solution of 48 mmol of the appropriate alkyl or aralkyl halide in a minimum volume of THF was added dropwise and the solution was allowed to warm to room temperature and was stirred overnight. A 50 mL portion of 2N aqueous HCl (100 mmol) was added and the two phase mixture was stirred vigorously until TLC analysis showed that hydrolysis of the imine was complete (2-8 h). The mixture was extracted with $Et_2O$ or EtOAc and the organic layer was washed with water, saturated aqueous $NaHCO_3$, and brine. After drying over $Na_2SO_4$ and concentration, the crude product was purified by either MPLC or vacuum distillation using a short path still.

Alternatively, a solution of 50 mmol of the appropriate cyclohexylimine in a minimum volume of THF was added dropwise under $N_2$ to an ice-cold stirring solution of 52.5 mmol of lithium diisopropylamide (LDA, generated by the addition of 55 mmol of diisopropylamine in 35 mL of THF to 52.5 mmol of a 1.6M hexanes solution of n-BuLi at $0°$ C.). After 30-45 min, a solution of 48 mmol of the appropriate alkyl or aralkyl halide in a minimum volume of THF was added dropwise and the mixture was allowed to warm to room temperature and was stirred overnight. A 75 mL portion of 2N aqueous HCl (150 mmol) was added and the two phase mixture was stirred vigorously until TLC analysis showed that hydrolysis of the imine was complete (4-24 h). The reaction mixture was worked up as described above.

Method B (RS step b): An ice-cold suspension of oil-free NaH (150 mmol) in 120 mL of a 1:1 mixture of benzene and DMF was treated, dropwise, with ethyl 2-cyclohexanonecarboxylate (145 mmol) in 60 mL of the same solvent mixture over a 30 min period. The mixture was stirred an additional 30 min and 140 mmol of the appropriate alkyl or aralkyl halide in a minimum amount of benzene was added dropwise. After stirring at room temperature for 2-3 days, 250 mL of $Et_2O$ was added and the organic solution was washed with water (3×100 mL) and brine. Drying ($Na_2SO_4$) and concentration gave the crude alkylated keto ester which was dissolved in 100 mL each of HOAc and 6N aqueous HCl and refluxed until TLC analysis showed that the hydrolysis/decarboxylation was complete (2-3 days). Most of the solvent was removed by rotary evaporation and the residue was partitioned between water (100 mL) and Et$_2$O (300 mL). The Et$_2$O layer was washed with brine, dried over Na$_2$SO$_4$, and concentrated to give the crude product which was purified as described in Method A above.

able) in 50 mL of THF was added. After 45 min, 27.5 mmol of methyl dimethoxyacetate was added and the mixture was allowed to warm slowly to room temperature. After stirring overnight, the resulting solution was cooled to 0° C. and acidified to pH 3-4 with 2N aqueous HCl. The mixture was diluted with Et$_2$O (200 mL) and washed with water and brine. After drying over Na$_2$SO$_4$, the solution was concentrated to give the crude

TABLE 1

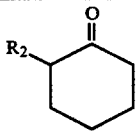

| Compound Number | Method | R$_2$ | bp (°C.) | Mass spectrum m/z [M + H]$^+$ |
|---|---|---|---|---|
| 85 | A | (1-Nap)—CH$_2$ | oil | 239 |
| 86 | B | (2-Cl—Ph)—CH$_2$ | 129-135 (0.4 Torr) | 223 |
| 87 | A | (2-Nap)—CH$_2$ | 180-190 (0.6 Torr) | 239 |
| 88 | A | (3-MeO—Ph)—CH$_2$ | 190-195 (4 Torr) | 219 |
| 89 | A | (3,4-di-MeO—Ph)—CH$_2$ | 180-187 (1 Torr) | 249 |
| 90 | A | (4-Cl—Ph)—CH$_2$ | 150-170 (0.1 Torr) | 223 |
| 91 | B | (4-F—Ph)—CH$_2$ | 110-125 (0.5 Torr) | 207 |
| 92 | A | (4-i-Pr—Ph)—CH$_2$ | 90-160 (0.1 Torr) | 231 |
| 93 | A | (4-Me—Ph)—CH$_2$ | oil | 203 |
| 94 | B | (4-MeO—Ph)—CH$_2$ | 155-170 (0.6 Torr) | 219 |
| 95 | A | (4-t-Bu—Ph)—CH$_2$ | 135-148 (0.5 Torr) | 245 |
| 96 | A | Ph—(CH$_2$)$_2$ | 124-130 (0.5 Torr) | 203 |
| 97 | A | Ph—(CH$_2$)$_3$ | 100-200 (0.8 Torr) | 217 |
| 98 | A | Ph—CH=CH—CH$_2$ | 160-170 (0.8 Torr) | 215 |

EXAMPLE 2

6-[(1,1'-Biphenyl-4-yl)methyl]-2-(2,2-dimethoxy-1-oxo-ethyl)cyclohexanone (CP 99, RS step c)

Diisopropylamine (38.8 mmol, 3.93 g, 5.4 mL) was added under N$_2$ to a −20° C. solution of 1.6M n-BuLi in hexanes (35.3 mmol, 22.0mL) and 30 mL of THF. After 15 min, the solution was cooled to −78° C. and 8.88 g (33.6 mmol) of Compound 84 in 50 mL of THF was added. After 45 min, 2.26 mL (18.5 mmol, 2.48 g) of methyl dimethoxyacetate was added and the mixture was allowed to warm slowly to room temperature and was stirred overnight. The resulting solution was cooled to 0° C. and acidified to pH 3-4 with 2N aqueous HCl. The mixture was diluted with Et$_2$O (200 mL) and washed with water and brine. After drying over Na$_2$SO$_4$, the solution was concentrated to give 11.5 g of a yellow oil. The crude product was purified by MPLC using a solvent gradient ranging from 1:6 to 1:5 EtOAc:hexanes to afford 5.94 g (96%) of the title compound as a waxy, white solid; $^1$H NMR (CDCl$_3$, 300 MHz) 1.4-2.8 (complex, 9), 3.33 (s, 3, minor tautomer), 3.37 (s, 3, minor tautomer), 3.42 (s, 6, major tautomer), 4.63 (s, 1, minor tautomer), 4.96 (s, 1, major tautomer), 7.2-7.6 (complex, 9); IR (KBr) 1739, 1704, 1601, 1584, 1488, 1444 cm$^{-1}$; MS (DCI) m/z 335 (base), 303. Anal. Calcd. for C$_{23}$H$_{26}$O$_4$: C, 75.38; H, 7.15. Found: C, 75.64; H, 7.39.

General procedure for the preparation of 6-substituted diketones shown in Table 2 (RS step c):

Diisopropylamine (57.8 mmol) was added under N$_2$ to a −20° C. solution of 52.5 mmol of a 1.6M hexanes solution of n-BuLi and 45 mL of THF. (Alternatively, 52.5 mmol of a 1.0M solution of LiN(SiMe$_3$)$_2$ in THF/cyclohexane was added to 25 mL of THF under N$_2$ at −20° C.) After 15 min, the solution was cooled to −78° C. and 50.0 mmol of the appropriately substituted cyclohexanone (from Table 1, or commercially availproduct, which was purified by MPLC.

TABLE 2

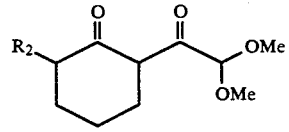

| Compound Number | R$_2$ | mp (°C.) | Mass spectrum m/z [MH-MeOH]$^+$ |
|---|---|---|---|
| 100 | (1-Nap)—CH$_2$ | oil | 309 |
| 101 | (2-Cl—Ph)—CH$_2$ | oil | 293 |
| 102 | (2-Et)Bu | oil | 225 |
| 103 | (2-Nap)—CH$_2$ | oil | 309 |
| 104 | (3-MeO—Ph)—CH$_2$ | oil | 289 |
| 105 | (3,4-di-MeO—Ph)—CH$_2$ | oil | 319 |
| 106 | (4-Cl—Ph)—CH$_2$ | oil | 293 |
| 107 | (4-F—Ph)—CH$_2$ | oil | 277 |
| 108 | (4-i-Pr—Ph)—CH$_2$ | oil | 301 |
| 109 | (4-Me-Ph)—CH$_2$ | oil | 273 |
| 110 | (4-MeO—Ph)—CH$_2$ | oil | 289 |
| 111 | (4-t-Bu—Ph)—CH$_2$ | oil | 315 |
| 112 | c-Hex | oil | 251 |
| 113 | Et | oil | 197 |
| 114 | Me | oil | 183 |
| 115 | n-Pr | oil | 211 |
| 116 | Ph | oil | 245 |
| 117 | Ph—CH$_2$ | oil | 259 |
| 118 | Ph—(CH$_2$)$_2$ | oil | 273 |
| 119 | Ph—(CH$_2$)$_3$ | oil | 287 |
| 120 | Ph—CH=CH—CH$_2$ | oil | 285 |
| 121 | s-Bu | oil | 225 |

EXAMPLE 3

7-[(1,1'-Biphenyl-4-yl)methyl]-2-(4-fluorophenyl)-4,5,6,7-tetrahydro-2H-indazole-3-carboxaldehyde (CP 122, RS step g) and
7-[(1,1'-Biphenyl-4-yl)methyl]-1-(4-fluorophenyl)-4,5,6,7-tetrahydro-1H-indazole-3-carboxaldehyde (CP 123 RS step g)

A solution of Compound 99 (20.2 mmol. 5.35 g) in 100 mL of absolute EtOH was treated with 1.91 g (23.3 mmol) of NaOAc and 3.45 g (21.2 mmol) of 4-fluorophenylhydrazine • HCl. After stirring overnight under N₂, the solvent was removed by rotary evaporation and the orange residue was dissolved in 100 mL of THF. A 50 mL portion of 1N aqueous HCl was added and the mixture was stirred and refluxed gently for 4 h. Et₂O (150 mL) was added after cooling and the organic layer was washed sequentially with water, saturated aqueous NaHCO₃, and brine. Drying over Na₂SO₄ and concentration afforded 6.74 g of an orange foam. The crude product was purified by MPLC using 1:9 EtOAc:hexanes to give 1.90 g (23%) of the 2-(4-fluorophenyl) isomer and 1.15 g (14%) of the 1-(4-fluorophenyl) isomer, each as an orange solid. The 2-(4-fluorophenyl) isomer was recrystallized from EtOAc:Et₂O to afford Compound 122 as a pale orange solid, m.p. 148°-150° C.; ¹H NMR (CDCl₃, 300 MHz) 1.6-2.0 (complex, 4), 2.72 (dd, 1, J=10.5, 13.5 Hz), 2.75-3.0 (complex), 3.15 (m, 1), 3.56 (dd, 1, J=4, 13.5 Hz), 7.2-7.7 (complex, 13), 9.87 (s, 1); IR (KBr) 1510, 1222 cm⁻¹; MS (DCI) m/z 411 (base). HRMS (EI) Calcd for C₂₇H₂₃FN₂O: 410.179428. Found: 410.175457.

The 1-(4-fluorophenyl) isomer was recrystallized from EtOAc:hexanes to provide analytically pure Compound 123 as an orange solid, m.p. 155-156; ¹H NMR (CDCl₃, 300 MHz) 1.7-1.9 (complex, 4), 2.46 (dd, 1, J=10.5, 13.5 Hz), 2.61 (dd, 1, J=4, 13.5 Hz), 2.73 (dt, 1, J=16.5, 8 Hz), 3.02 (dt, 1, J=16.5, 4 Hz), 3.30 (m, 1), 6.89 (d, 2, J=8 Hz), 7.2-7.6 (complex, 11), 10.08 (s, 1); IR (KBr) 1691, 1512 cm⁻¹; MS (DCI) m/z 411 (base). Anal. Calcd. for C₂₇H₂₃FN₂O: C, 79.00; H, 5.65; N, 6.82. Found: C, 79.22; H, 5.54; N, 6.61.

General procedure for the preparation of 7-substituted 4,5,6,7-tetrahydroindazole-3-carboxaldehydes shown in Tables 3A and 3B (RS step g):

A solution of 10 mmol of the appropriately substituted diketone from Table 2 in 100 mL of absolute EtOH or MeOH was treated with 11.5 mmol of a base (NaOAc, Et₃N, or pyridine) and 10.5 mmol of the appropriately substituted hydrazine hydrochloride. After stirring overnight under N₂, the solvent was removed by rotary evaporation and the residue was dissolved in 50 mL of THF. A 25 mL portion of 1N aqueous HCl was added and the mixture was stirred and refluxed gently for 4 h. After cooling, 100 mL of Et₂O was added and the organic layer was washed sequentially with water, saturated aqueous NaHCO₃, and brine. Drying over Na₂SO₄ and concentration afforded the crude product as a mixture of 2-aryl and 1-aryl isomers in ratios ranging from 1:1 to 1:3. The crude mixture was purified by recrystallization and/or MPLC; the 2-aryl isomer eluted before the 1-aryl isomer in all cases.

TABLE 3A

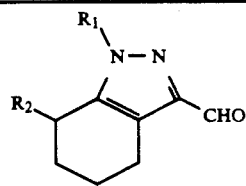

| Compound Number | R₁ | R₂ | mp (°C.) | Mass Spectrum [M + H]⁺ |
|---|---|---|---|---|
| 124 | 4-F—Ph | (1-Nap)—CH₂ | 183-184 | 385 |
| 125 | 4-F—Ph | (2-Cl—Ph)—CH₂ | 137-138 | 369 |
| 126 | 4-F—Ph | (2-Et)Bu | 121-122 | 329 |
| 127 | 4-F—Ph | (2-Nap)—CH₂ | foam | 385 |
| 128 | 4-F—Ph | (3-MeO—Ph)—CH₂ | 93-94 | 365 |
| 129 | 4-F—Ph | (3,4-di-MeO—Ph)—CH₂ | 117-119 | 395 |
| 130 | 4-F—Ph | (4-Cl—Ph)—CH₂ | 134-135 | 369 |
| 131 | 4-F—Ph | (4-F—Ph)—CH₂ | 128-131 | 353 |
| 132 | 4-F—Ph | (4-i-Pr—Ph)—CH₂ | 112-113 | 377 |
| 133 | 4-F—Ph | (4-Me—Ph)—CH₂ | 117-118 | 349 |
| 134 | 4-F—Ph | (4-MeO—Ph)—CH₂ | 104-107 | 365 |
| 135 | 4-F—Ph | (4-t-Bu—Ph)—CH₂ | 139-140 | 391 |
| 136 | 4-F—Ph | c-Hex | 119-121 | 327 |
| 137 | 4-F—Ph | Et | 95-97 | 273 |
| 138 | 4-F—Ph | Me | 124-125 | 259 |
| 139 | 4-F—Ph | n-Pr | oil | 287 |
| 140 | 4-F—Ph | Ph | 71-73 | 321 |
| 141 | 4-F—Ph | Ph—CH₂ | 144-145 | 335 |
| 142 | 4-F—Ph | Ph—(CH₂)₂ | 97-99 | 349 |
| 143 | 4-F—Ph | Ph—(CH₂)₃ | oil | 363 |
| 144 | 4-F—Ph | Ph—CH=CH—CH₂ | 106-108 | 361 |
| 145 | 4-F—Ph | s-Bu | 86-89 | 301 |
| 296 | t-Bu | (1-Nap)—CH₂ | 119-120 | 347 |

TABLE 3B

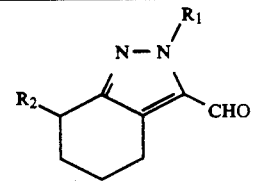

| Compound Number | R₁ | R₂ | mp (°C.) | Mass Spectrum [M + H]⁺ |
|---|---|---|---|---|
| 146 | 4-F—Ph | (1-Nap)—CH₂ | 116-117 | 385 |
| 147 | 4-F—Ph | (2-Cl—Ph)—CH₂ | glass | 369 |
| 297 | 4-F—Ph | (2-Et)Bu | foam | 329 |
| 148 | 4-F—Ph | (2-Nap)—CH₂ | 122-123 | 385 |
| 149 | 4-F—Ph | (3-MeO—Ph)—CH₂ | foam | 365 |
| 150 | 4-F—Ph | (3,4-di-MeO—Ph)—CH₂ | 109-110 | 395 |
| 151 | 4-F—Ph | (4-Cl—Ph)—CH₂ | 126-128 | 369 |
| 152 | 4-F—Ph | (4-F—Ph)—CH₂ | oil | 353 |
| 153 | 4-F—Ph | (4-i-Pr—Ph)—CH₂ | oil | 377 |
| 154 | 4-F—Ph | (4-Me—Ph)—CH₂ | foam | 349 |
| 155 | 4-F—Ph | (4-MeO—Ph)—CH₂ | oil | 365 |
| 156 | 4-F—Ph | (4-t-Bu—Ph)—CH₂ | 124-125 | 391 |
| 157 | 4-F—Ph | c-Hex | oil | 327 |
| 158 | 4-F—Ph | Et | 72-74 | 273 |
| 159 | 4-F—Ph | Me | 79-80 | 259 |
| 160 | 4-F—Ph | n-Pr | 50-53 | 287 |
| 161 | 4-F—Ph | Ph | 139-140 | 321 |
| 162 | 4-F—Ph | Ph—CH₂ | 99-100 | 335 |
| 163 | 4-F—Ph | Ph—(CH₂)₂ | 89-90 | 349 |
| 164 | 4-F—Ph | Ph—(CH₂)₃ | 100-102 | 363 |
| 165 | 4-F—Ph | Ph—CH=CH—CH₂ | 104-105 | 361 |
| 166 | 4-F—Ph | s-Bu | oil | 301 |
| 298 | t-Bu | (1-Nap)—CH₂ | 142-143 | 347 |

EXAMPLE 4

3-Acetoxymethyl-2-(4-fluorophenyl)-4,5,6,7-tetrahydro-2H-indazole (CP 167, RS step h)

$Et_3N$ (0.717 mL, 0.520 g, 5.14 mmol) was added to a stirring suspension of 1.00 g (5.04 mmol) of 2-acetoxyacetylcyclohexanone (Dolmazon, R.; Gelin, S. *J. Heterocyclic Chem.*, 1982, 19, 117–121) and 0.820 g (5.04 mmol) of 4-fluorophenylhydrazine•HCl in 20 mL of absolute EtOH. The resulting solution was stirred under $N_2$ for 4 h at room temperature and refluxed for 6 h. The mixture was concentrated and the residue was partitioned between 100 mL of $Et_2O$ and 50 mL of dilute aqueous HCl. The $Et_2O$ layer was washed with water, saturated aqueous $NaHCO_3$, and brine. After drying over $Na_2SO_4$, the solution was concentrated to give 1.43 g of light brown solid. Recrystallization from EtOAc:hexanes afforded 0.753 g (52%) of the title compound as a white solid, m.p. 128.5°–129.5° C.; $^1$H NMR ($CDCl_3$, 400 MHz) 1.85 (m, 4), 2.07 (s, 3), 2.60 (t, 2, J=6 Hz), 2.73 (t, 2, J=6 Hz), 5.00 (s, 2), 7.15 (t, 2, J=9 Hz), 7.45 (dd, 2, J=5, 9 Hz); IR (KBr) 1740, 1220 cm$^{-1}$; MS (DCI) m/z 289 (base), 228. Anal. Calcd. for $C_{16}H_{17}FN_2O_2$: C, 66.65; H, 5.94; N, 9.72. Found: C, 66.74; H, 5.89; N, 9.61.

General procedure for the preparation of acetates shown in Table 4 (RS step h):

A mixture of 10 mmol of the appropriate 2-acetoxyacetylcycloalkanone (2-acetoxyacetylcyclopentanone, Dolmazon, R. *J. Heterocyclic Chem.*, 1988, 25, 751–7; 2-acetoxyacetylcyclohexanone, Dolmazon, R.; Gelin, S. *J. Heterocyclic Chem.*, 1982, 19, 117–21), 10.5 mmol of $Et_3N$, and 10 mmol of appropriately substituted hydrazine in 40 mL of absolute EtOH was stirred under $N_2$ for 4–5 h and refluxed for 6–8 h. The solvent was evaporated and the resulting residue was partitioned between $Et_2O$ and 0.1N HCl. The $Et_2O$ layer was washed with water, saturated aqueous $NaHCO_3$, and brine. After drying over $Na_2SO_4$, the solution was concentrated and the crude product was purified by recrystallization and/or MPLC. The 2-acetoxyacetylcyclopentanone reaction afforded a 9:1 mixture of 1-aryl:2-aryl isomers, while the 2-acetoxyacetylcyclohexanone reaction gave only the 2-aryl isomer.

TABLE 4

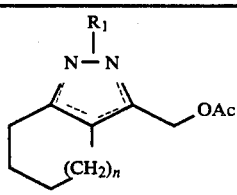

| Compound Number | n | $R_1$ | mp (°C.) | Mass Spectrum [M + H]$^+$ |
|---|---|---|---|---|
| 168 | 0 | 1-(4-F—Ph) | 85–86 | 275 |
| 169 | 0 | 2-(4-F—Ph) | 87–88 | 275 |
| 170 | 1 | 2-(4-Cl—Ph) | oil | 305 |

EXAMPLE 5

2-(4-Fluorophenyl)-4,5,6,7-tetrahydro-2H-indazole-3-methanol (CP 171, RS step i)

Compound 167 (24.3 mmol, 7.00 g) was dissolved in 125 mL of MeOH and stirred while 26.7 mL of 1N aqueous NaOH was added. After 30 min the resulting cloudy suspension was concentrated and partitioned between 200 mL of EtOAc and 100 mL of water. The organic layer was washed with water and brine and was dried over $Na_2SO_4$. The solution was concentrated to give 5.85 g of orange solid. Recrystallization from EtOAc gave 4.08 g (68%) of the title compound as off-white crystals, m.p. 163°–164° C.; $^1$H NMR ($CDCl_3$, 400 MHz) 1.80 (m, 4), 2.52 (t, 1, J=5 Hz), 2.86 (t, 2, J=6 Hz), 2.71 (t, 2, J=6 Hz), 4.52 (d, 2, J=5 Hz), 7.12 (2, t, J=9 Hz), 7.58 (dd, 2, J=5, 9 Hz); $^{13}$C NMR (DMSO-$d_6$, 25 MHz) 19.8, 23.0 (triple), 52.1, 115.7 (d, $J_{C-F}$=23 Hz), 116.6, 125.2 (d, $J_{C-F}$=8 Hz), 136.5, 137.9, 148.8, 160.6 (d, $J_{C-F}$=244 Hz); IR (KBr) 3200 (broad), 1510 cm$^{-1}$; MS (DCI) m/z 247 (base). Anal. Calcd. for $C_{14}H_{15}FN_2O$: C, 68.28; H, 6.14; N, 11.37. Found: C, 68.47; H, 6.02; N, 11.35.

General procedure for the preparation of alcohols shown in Table 5 (RS step i):

The appropriate acetate from Table 4 (10 mmol) was dissolved in 50 mL of MeOH and stirred while 11 mmol of 1N aqueous NaOH was added. The resulting suspension was stirred 0.5–24 h and worked up by one of two methods. In the first method, the mixture was concentrated and partitioned between water and solvent. The organic phase was washed with water and brine, dried over $Na_2SO_4$, and concentrated. Alternatively, the reaction mixture was filtered to remove the solids and the filtrate was treated with water to precipitate the remaining product. The combined solids were dissolved in $CHCl_3$, washed with brine, and concentrated. The crude product was purified by recrystallization or a combination of recrystallization and MPLC.

TABLE 5

| Compound Number | n | $R_1$ | mp (°C.) | Mass Spectrum [M + H]$^+$ |
|---|---|---|---|---|
| 172 | 0 | 1-(4-F—Ph) | 85–86 | 233 |
| 173 | 0 | 2-(4-F—Ph) | 170–171 | 233 |
| 174 | 1 | 2-(4-Cl—Ph) | 184.5–185 | 263 |

EXAMPLE 6

2-(4-Fluorophenyl)-2,4,5,6,7,8-hexahydrocycloheptapyrazole-3-methanol (CP 175, RS step e, followed by RS step k)

A solution of 2.80 g (25 mmol) of cycloheptanone and 4.71 g (25 mmol) of ethyl (tetrahydropyranyloxy)acetate (Ireland, R. E.; Wipf, P. *Tetrahedron Lett.*, 1989, 30, 919–22) in 20 mL of $Et_2O$ was added over the course of 1 h to an ice-cold, stirring mixture of hexane-washed NaH and 0.12 mL (2 mmol, 0.092 g) of absolute EtOH in 10 mL of $Et_2O$ under $N_2$. The light brown mixture was allowed to warm to room temperature and was stirred overnight. MeOH (5 mL) was added and the solution was poured onto 200 mL of saturated aqueous $NH_4Cl$. After acidification to pH 2 with 1N aqueous HCl, the mixture was extracted with $Et_2O$. The organic layer was washed with brine, dried over $Na_2SO_4$, and concentrated to give 5.61 g of crude 2-[(tetrahydropyranyloxy)acetyl]cycloheptanone as a light brown oil.

The crude diketone was dissolved in 60 mL of absolute EtOH and combined with 3.07 mL (22 mmol, 2.23 g) of Et$_3$N and 3.45 g (21.1 mmol) of 4-fluorophenylhydrazine·HCl. The resulting solution was stirred under N$_2$ overnight and refluxed for 4 h. A 30 mL portion of 1N aqueous HCl was added and the mixture was refluxed for an additional hour. The mixture was cooled and extracted with 200 mL of Et$_2$O. The organic phase was washed with water, saturated aqueous NaHCO$_3$, and brine and dried over Na$_2$SO$_4$. The solution was concentrated to give 5.50 g of a 1.2:1 mixture of 1-(4-fluorophenyl)-1,4,5,6,7,8-hexahydrocycloheptapyrazole-3-methanol and the title compound as a brown oil. The crude product was crystallized from EtOAc:Et$_2$O to afford 0.97 g (18%) of the title compound as an off-white solid, m.p. 177°–178° C.; $^1$H NMR (CDCl$_3$, 300 MHz) 1.72 (m, 4), 1.85 (m, 2), 2.60 (m, 2), 2.80 (m, 2), 4.51 (d, 2, J=5 Hz), 7.15 (m, 2), 7.60 (m, 2); IR (KBr) 3240 (broad), 1513, 1223 cm$^{-1}$; MS (DCI) m/z 261 (base). Anal. Calcd. for C$_{15}$H$_{17}$FN$_2$: C, 69.21; H, 6.58; N, 10.76. Found: C, 69.15; H, 6.77; N, 10.63.

EXAMPLE 7

Ethyl 2,4,5,6,7,8-hexahydrocycloheptapyrazole-3-carboxylate (CP 176, RS step f, followed by RS step l)

Hydrazine hydrate (30.3 mmol, 1.52 g, 1.47 mL) was added dropwise under N$_2$ to a stirring solution of ethyl α,2-dioxocycloheptaneacetate (Tsuboi, S.; Nishiyama, E.; Furutani, H.; Utaka, M.; Takeda, A. *J. Org. Chem.*, 1987, 52, 1359–62) in 60 mL of MeOH. The reaction mixture, which had become warm during the addition, was allowed to cool to room temperature and was stirred overnight. The solvent was evaporated and the resulting oil was dissolved in CH$_2$Cl$_2$ and washed with water and brine. After drying over Na$_2$SO$_4$, the solution was concentrated to give 6.36 g of pale yellow solid. Recrystallization from EtOAc:hexanes afforded 3.44 g (52%) of the title compound as a white solid, m.p. 90°–92° C.; $^1$H NMR (CDCl$_3$, 300 MHz) 1.38 (t, 3, J=7 Hz), 1.67 (m, 4), 1.84 (m, 2), 2.80 (m, 2), 2.93 (m, 2), 4.37 (q, 2, J=7 Hz), 7.0 (broad s, 1); IR (KBr) 1719 cm$^{-1}$; MS (DCI) m/z 209 (base). Anal. Calcd. for C$_{11}$H$_{16}$N$_2$O$_2$: C, 63.44; H, 7.74; N, 13.45. Found: C, 63.48; H, 7.76; N, 13.64.

EXAMPLE 8

Ethyl 2-(4-fluorobenzyl)-2,4,5,6,7,8-hexahydrocycloheptapyrazole-3-carboxylate (CP 177, RS step m) and ethyl 1-(4-fluorobenzyl)-1,4,5,6,7,8-hexahydrocycloheptapyrazole-3-carboxylate (CP 178, RS step m)

A solution of 7.90 g (37.9 mmol) of Compound 176 in 35 mL of DMF was added dropwise under N$_2$ to a suspension of hexane-washed NaH (41.7 mol, 1.67 g of a 60% oil suspension) in 20 mL of DMF. When the addition was complete, the mixture was heated at 140° C. with an oil bath for 15 min. A solution of 5.00 mL (41.7 mmol, 6.03 g) of 4-fluorobenzyl chloride in 5 mL of DMF was added and the mixture was heated for an additional 30 min. After cooling, 400 mL of Et$_2$O was added and the solution was poured onto 250 mL of saturated aqueous NH$_4$Cl. The aqueous layer was extracted with two 50 mL portions of Et$_2$O and the combined organic phases were washed with three 100 mL portions of water and once with brine. The organic solution was dried over Na$_2$SO$_4$ and concentrated to give 11.9 g of a 1:1 mixture of the title compounds as a yellow oil. Purification by MPLC afforded, in the earlier fractions, 3.85 g (32%) of pure 2-(4-fluorobenzyl) isomer as a colorless oil; $^1$H NMR (CDCl$_3$, 100 MHz) 1.31 (t, 3, J=7 Hz), 1.70 (m, 6), 2.83 (m, 4), 4.29 (q, 2, J=7 Hz), 5.58 (s, 2), 6.9–7.4 (complex, 4). The later-eluting fractions contained 4.94 g (42%) of the 1-(4-fluorobenzyl) isomer as a colorless oil; $^1$H NMR (CDCl$_3$, 100 MHz) 1.40 (t, 3, J=7 Hz), 1.4–2.0 (complex, 6), 2.55 (m, 2), 2.95 (m, 2), 4.41 (q, 2, J=7 Hz), 5.35 (s, 2), 7.00 (m, 4).

EXAMPLE 9

2-(4-Fluorobenzyl)-2,4,5,6,7,8-hexahydrocycloheptapyrazole-3-methanol (CP 179, RS step n)

A solution of 1.43 g (4.52 mmol) of Compound 177 in 13 mL of THF under N$_2$ was added dropwise over a 10 min period to an ice cold suspension of 0.113 g (2.83 mmol) of LiAlH$_4$ in 7 mL of THF. After 30 min in the cold, the suspension was allowed to warm to room temperature and was stirred for 2 h. Et$_2$O (50 mL) was added, followed sequentially by 0.12 mL of water, 0.12 mL of 15% aqueous NaOH, and 0.36 mL of water, dropwise over a 1 h period. The white suspension was stirred overnight, treated with MgSO$_4$, and stirred 30 min more. The solids were removed by filtration and were washed with CH$_2$Cl$_2$. The combined filtrates were concentrated to afford 1.24 g of a white solid, which was recrystallized to give 0.998 g (80%) of the title compound as white needles, m.p. 156°–157° C.; $^1$H NMR (CDCl$_3$, 300 MHz) 1.55–1.70 (complex, 7), 1.82 (m, 2), 2.47 (m, 2), 2.74 (m, 2), 4.48 (d, 2, J=6 Hz), 5.27 (s, 2), 6.98 (t, 2, J=7 Hz), 7.12 (m, 2); IR (KBr) 3170 (broad), 1517, 1231, 1016 cm$^{-1}$; MS (DCI) m/z 275 (base), 257. Anal. Calcd. for C$_{16}$H$_{19}$FN$_2$O: C, 70.05; H, 6.98; N, 10.21. Found: C, 69.98; H, 6.98; N, 10.28.

EXAMPLE 10

1-(4-Fluorobenzyl)-1,4,5,6,7,8-hexahydrocycloheptapyrazole-3-methanol (CP 180, RS step n)

Following the procedure described above, 4.82 mmol (15.23 g) of Compound 178 gave 4.12 g (98%) of the title compound as an amber oil, which was used without purification; $^1$H NMR (CDCl$_3$, 100 MHz) 1.70 (m, 6), 2.57 (m, 4), 3.0 (broad s, 1), 4.59 (d, 2, J=6 Hz), 5.20 (s, 2), 7.00 (m, 4).

EXAMPLE 11

2-(4-Fluorophenyl)-4,5,6,7-tetrahydro-2H-indazole-3-carboxaldehyde (CP 181, RS step j)

Pyridinium chlorochromate (22.0 mmol, 4.74 g) was suspended in 50 ml of CH$_2$Cl$_2$. Compound 171 (14.8 mmol, 3.64 g) was added in small portions over a 5 min period and the resulting suspension was stirred at room temperature for 4 h. A 300 mL portion of Et$_2$O was added and the mixture was filtered through a pad of Florisil. The tarry residue remaining in the flask was sonicated twice with 100 mL of Et$_2$O and the organic solutions were also filtered through Florisil. The Florisil pad was washed thoroughly with Et$_2$O and the combined organic solutions were dried over Na$_2$SO$_4$ and concentrated to give 3.57 g of an off-white solid. The crude product was recrystallized from Et$_2$O:hexanes to give 1.71 g (42%) of white crystals, m.p. 80°–81° C. (the mother liquors were concentrated to give 1.67 g (47%) of a white solid which was judged to be pure enough to carry on); $^1$H NMR (CDCl$_3$, 400 MHz) 1.85 (m, 4), 2.77 (t, 2, J=6 Hz), 2.88 (t, 2, J=6 Hz), 7.20 (m, 2), 7.45 (m, 2), 9.86 (s, 1); IR (KBr) 1670, 1575 cm$^{-1}$; MS (DCI) m/z 245 (base). Anal. Calcd. for C$_{14}$H$_{13}$FN$_2$O: C, 68.84; H, 5.36; N, 11.47. Found: C, 68.79; H, 5.40; N, 11.39.

General procedure for the preparation of aldehydes shown in Table 6 (RS step j):

Method A: MnO$_2$ (100–120 mmol) was added in one portion to a stirring suspension of 10 mmol of the alcohol from Example 10 in 60 mL of benzene. The mixture was refluxed gently under N$_2$ until TLC analysis indicated that the starting material was completely consumed. After cooling, the slurry was filtered through a Celite pad and the black solids were washed with 250 mL of CH$_2$Cl$_2$. The filtrate was concentrated and the crude product was purified by MPLC or recrystallization.

Method B: To a stirring suspension of pyridinium chlorochromate (10 mmol) in 25 mL of CH$_2$Cl$_2$ was added, in approximately five portions, the appropriately substituted alcohol from Table 5 or Examples 5, 6, or 9, as a solid. The resulting suspension was stirred for 2–4 h at room temperature. Et$_2$O (150 mL) was added and the mixture was sonicated for 5–10 min. The supernatant was decanted through a pad of Florisil and the remaining solids were sonicated twice with 50 mL portions of Et$_2$O, which in turn were filtered. The Florisil pad was washed thoroughly with Et$_2$O and the combined filtrates were concentrated to give the crude product, which was purified by recrystallization.

TABLE 6

| Compound Number | Method | n | R$_1$ | mp (°C.) | Mass spectrum m/z [M + H]$^+$ |
|---|---|---|---|---|---|
| 182 | B | 0 | 1-(4-F—Ph) | 122–123 | 231 |
| 183 | B | 0 | 2-(4-F—Ph) | 79–80 | 231 |
| 184 | B | 1 | 2-(4-Cl—Ph) | 93–94 | 261 |
| 185 | B | 2 | 2-(4-F—Ph) | oil | 259 |
| 186 | A | 2 | 1-(4-F—Ph—CH$_2$) | oil | 273 |
| 187 | B | 2 | 2-(4-F—Ph—CH$_2$) | oil | 273 |

EXAMPLE 12

Methyl (E)-7-[7-[(1,1'-Biphenyl-4-yl)methyl]-2-(4-fluorophenyl)-4,5,6,7-tetrahydro-2H-indazol-3-yl]-3-hydroxy-5-oxo-6-heptenoate (CP 188, RS step t)

Compound 122 (2.68 mmol, 1.10 g), LiCl (3.08 mmol, 0.131 g), and 1.18 g (3.08 mmol) of methyl 3-[(t-butyldimethylsilyl)oxy]-6-(dimethoxyphosphinyl)-5-oxohexanoate (Theisen, P. D.; Heathcock, C. H. *J. Org. Chem.*, 1988, 53, 2374–81) were combined in 15 mL of CH$_3$CN. DBU (2.95 mmol, 0.449 g, 0.441 mL) was added and the resulting clear, orange solution was stirred under N$_2$ for 6 h. The mixture was diluted with 100 mL of Et$_2$O and washed successively with 50 mL of 5% aqueous NaHSO$_4$, water, and brine. After drying over Na$_2$SO$_4$, the solution was concentrated to give 2.00 g of orange oil. The crude mixture was dissolved in 25 mL of CH$_3$CN, treated with 2.5 mL of 48% aqueous HF, and stirred for 5 h. Et$_2$O (100 mL) was added and the acid was quenched by careful addition of saturated aqueous NaHCO$_3$. The ethereal solution was washed with brine, dried over Na$_2$SO$_4$, and concentrated to give 1.54 g of orange foam. The crude product was purified by MPLC using 1:2 EtOAc:hexanes to afford 0.22 g (15%) of the title compound as a yellow solid and an additional 0.50 g (34%) as a pale yellow solid which crystallized directly from the chromatography fractions, m.p. 137°–138° C.; $^1$H NMR (CDCl$_3$, 300 MHz) 1.4–2.1 (complex, 4), 2.56 (d, 2, J=6 Hz), 2.71 (m, 3), 2.80 (d, 2, J=6 Hz), 3.15 (m, 1), 3.47 (d, 1, J=4 Hz), 3.56 (dd, 1, J=4, 13.5 Hz), 3.71 (s, 3), 4.52 (m, 1), 6.51 (d, 1, J=16 Hz), 7.1–7.7 (complex, 14); IR (KBr) 3450 (broad), 1734, 1603, 1512 cm$^{-1}$; MS (DCI) m/z 553, 451 (base). Anal. Calcd. for C$_{34}$H$_{33}$FN$_2$O$_4$: C, 73.89; H, 6.02; N, 5.07. Found: C, 73.94; H, 6.01; N, 5.03.

General procedure for the preparation of 7-substituted (E)-3-hydroxy-5-oxo-6-heptenoates shown in Table 7 (RS step t):

The appropriately substituted aldehyde (10 mmol) from Table 3A or 3B was combined with 11.5 mmol of LiCl and 11.5 mmol of methyl 3-[(t-butyldimethylsilyl)oxy]-6-(dimethoxyphosphinyl)-5-oxohexanoate in 25 mL of CH$_3$CN. DBU (11 mmol) was added and the resulting clear solution was stirred for 4–6 h, becoming slightly cloudy during that time. The mixture was diluted with 100 mL of Et$_2$O and washed successively with 100 mL of 5% aqueous NaHSO$_4$, water, and brine. After drying over Na$_2$SO$_4$, the solution was concentrated to give the crude silyloxy keto ester. The crude residue was dissolved in 100 mL of CH$_3$CN and was treated with 10 mL of 48% aqueous HF. After TLC analysis indicated complete consumption of silyloxy keto ester, 200 mL of Et$_2$O was added and the HF was quenched by careful addition of saturated aqueous NaHCO$_3$. The ethereal solution was washed with brine, dried over Na$_2$SO$_4$, and concentrated to give the crude product, which was purified by MPLC.

TABLE 7

| Compound Number | R$_1$ | R$_2$ | mp (°C.) | Mass Spectrum m/z [M + H]$^+$ |
|---|---|---|---|---|
| 189 | 1-(4-F—Ph) | Ph—(CH$_2$)$_2$ | oil | 491 |
| 190 | 2-(4-F—Ph) | (1-Nap)—CH$_2$ | foam | 527 |
| 191 | 2-(4-F—Ph) | (2-Nap)—CH$_2$ | foam | 527 |
| 192 | 2-(4-F—Ph) | (4-i-Pr—Ph)—CH$_2$ | oil | 519 |
| 193 | 2-(4-F—Ph) | (4-t-Bu—Ph)—CH$_2$ | foam | 533 |
| 194 | 2-(4-F—Ph) | Ph | foam | 463 |
| 195 | 2-(4-F—Ph) | Ph—CH=CH—CH$_2$ | oil | 503 |

EXAMPLE 13

Methyl (E)-(3RS,5SR)-7-[7-[(1,1'-Biphenyl-4-yl)methyl]-2-(4-fluorophenyl)-4,5,6,7-tetrahydro-2H-indazol-3-yl]-3,5-dihydroxy-6-heptenoate (CP 39, RS step u)

Compound 188 (1.21 mmol, 0.67 g) was dissolved in 1.5 mL of MeOH and 5 mL of THF and treated, dropwise, with 1.33 mL (1.33 mmol) of a 1.0M solution of Et$_3$B in THF. Air (5 mL) was bubbled into the solution via syringe and the resulting solution was stirred under N$_2$ for 2 h and then cooled to $-78°$ C. After addition of solid NaBH$_4$ in one portion, the mixture was allowed to warm slowly to room temperature and was stirred overnight. Et$_2$O (100 mL) and saturated aqueous NH$_4$Cl (50 mL) were added. The ethereal solution was washed with brine, dried over Na$_2$SO$_4$, and concentrated to give a yellow oil. The oil was dissolved in MeOH, stirred under air overnight, and concentrated to provide 0.74 g of pale yellow foam. Purification by MPLC using 45:55 EtOAc:hexanes afforded a white foam which crystallized upon addition of Et$_2$O, giving 281 mg (42%) of the title compound as a white solid, m.p. 118°–119° C. (the mother liquors gave 77 mg (12%) of additional product as a white foam); $^1$H NMR (CDCl$_3$, 300 MHz) 1.4–2.0 (complex, 6), 2.49 (d, 2, J=6 Hz), 2.6–2.8 (complex, 3), 3.10 (m, 1), 3.56 (dt, 1, J=13.5, 3.5 Hz), 3.62 (s, 1), 3.71 (s, 3), 3.78 (s, 1), 4.28 (m, 1), 4.48 (m, 1), 6.01 (dd, 1, J=6, 16 Hz), 6.45 (d, 1, J=16 Hz); $^{13}$C NMR (CDCl$_3$, 75 MHz) 21.6, 22.8, 27.9, 36.2, 40.3, 41.3, 42.7, 51.9, 68.3, 72.5, 115.7, 116.0 (J$_{C-F}$=23 Hz), 118.0, 127.0, 127.3 (J$_{C-F}$=38 Hz), 128.7, 129.8, 135.0, 135.3, 136.1, 138.8, 139.8, 141.1, 153.3, 161.7 (J$_{C-F}$=247 Hz), 172.9; IR (KBr) 3400 (broad), 1734, 1513 cm$^{-1}$; MS (DCI) m/z 555 (base), 537, 523. Anal. Calcd. for C$_{34}$H$_{35}$FN$_2$O$_4$: C, 73.63; H, 6.36; N, 5.05. Found: C, 73.33; H, 6.60; N, 5.06.

General procedure for the preparation of 7-substituted (E)-(3RS,5SR)-3,5-dihydroxy-6-heptenoates shown in Table 8 (RS step u):

The appropriately substituted hydroxy keto ester from Table 7 (10 mmol), dissolved in 10 mL of MeOH and 30 mL of THF, was treated with 11 mmol of a 1.0M THF solution of Et$_3$B. Air (about 20 mL) was bubbled into the solution via syringe and the resulting solution was stirred under N$_2$ for 2 h. After cooling to $-78°$ C., the solution was treated with 11 mmol of solid NaBH$_4$ in one portion, causing some gas evolution. The mixture was allowed to warm slowly to room temperature and was stirred overnight. Saturated aqueous NH$_4$Cl was added and the mixture was extracted with Et$_2$O. The organic extracts were washed with brine, dried over Na$_2$SO$_4$, and concentrated to dryness. The residue, which smelled of excess Et$_3$B, was then dissolved in MeOH and stirred vigorously under air until TLC analysis showed complete conversion of the boron intermediates to the desired product (4–24 h). The MeOH was removed by rotary evaporation and the crude material was purified by MPLC.

TABLE 8

| Compound Number | R$^1$ | R$_2$ | mp (°C.) | Mass Spectrum m/z [M + H]$^+$ |
|---|---|---|---|---|
| 40 | 1-(4-F—Ph) | Ph—(CH$_2$)$_2$ | foam | 493 |
| 41 | 2-(4-F—Ph) | (1-Nap)—CH$_2$ | foam | 529 |
| 42 | 2-(4-F—Ph) | (2-Nap)—CH$_2$ | foam | 529 |
| 43 | 2-(4-F—Ph) | (4-i-Pr—Ph)—CH$_2$ | foam | 521 |
| 44 | 2-(4-F—Ph) | (4-t-Bu—Ph)—CH$_2$ | foam | 535 |
| 45 | 2-(4-F—Ph) | Ph | foam | 465 |
| 46 | 2-(4-F—Ph) | Ph—CH=CH—CH$_2$ | oil | 505 |

EXAMPLE 14

(E)-(3RS,5SR)-7-[7-[(1,1'-Biphenyl-4-yl)methyl]-2-(4-fluorophenyl)-4,5,6,7-tetrahydro-2H-indazol-3-yl]-3,5-dihydroxy-6-heptenoic acid•Sodium salt•Dihydrate (CP 1, RS step v)

Aqueous NaOH (0.25 N, 0.392 mmol, 1.57 mL) was added slowly to an ice-cold solution of Compound 39 (0.400 mmol, 222 mg) in 10 mL of MeOH. When the addition was complete, the solution was allowed to warm to room temperature and stirred for 2 h. The solution was concentrated to dryness using a rotary evaporator and the residue was dissolved in 40 mL of water. The slightly cloudy solution was suction filtered through a coarse frit, frozen in a $-78°$ C. bath, and lyophilized. The product was dried in a vacuum oven over Drierite to provide 219 mg (93%) of the title compound as a fluffy, white solid; $^1$H NMR (DMSO-d$_6$, 400 MHz) 1.3–2.0 (complex, 7), 2.05 (dd, 1, J=4, 15 Hz), 2.4–2.7 (complex, 4), 3.01 (m, 1), 3.40 (m, 1), 3.75 (m, 1), 4.26 (m, 1), 5.13 (broad s, 1), 6.07 (dd, 1, J=5, 16 Hz), 6.36 (d, 1, J=16 Hz), 7.2–7.7 (complex, 13); IR (KBr) 3400 (broad), 1577, 1513 cm$^{-1}$; MS (FAB+) m/z 535, 563, 541, 167, 115 (base). Anal. Calcd. for C$_{33}$H$_{32}$FN$_2$NaO$_4$•2 H$_2$O: C, 66.21; H, 6.06; N, 4.68. Found: C, 66.39; H, 5.67; N, 4.62.

General procedure for the preparation of 7-substituted (E)-(3RS,5SR)-3,5-dihydroxy-6-heptenoic acid sodium salts shown in Tables 9A and 9B (RS step v)

Aqueous NaOH (0.25 N, 0.98 mmol) was added slowly to an ice-cold methanolic solution (15 mL) of 1.0 mmol of the appropriately substituted dihydroxy ester of Table 8, 13A, or 13B or Example 20. When the addition was complete, the solution was allowed to warm to room temperature and stir for 2 h until TLC analysis indicated that nearly all starting material had been consumed. The solution was concentrated to dryness using a rotary evaporator and the residue was dissolved in 40 mL of water. The slightly cloudy solution was suction filtered through a coarse frit, frozen in a −78° C. bath, and lyophilized. The product was dried in a vacuum oven over Drierite to provide the desired sodium salt as a white, fluffy powder.

in an ice bath and Compound 162 (2.75 mmol, 0.92 g) in 10 mL of THF was added dropwise. The mixture was allowed to warm to room temperature and was stirred overnight. Saturated aqueous NH$_4$Cl (50 mL) was

TABLE 9A

| Compound Number | n | $R_1$ | $R_2$ | Mass Spectrum m/z [M + H]$^+$ |
|---|---|---|---|---|
| 2 | 0 | 4-F—Ph | H | 383 |
| 3 | 1 | 4-F—Ph | (4-F—Ph)—CH$_2$ | 505 |
| 4 | 1 | 4-F—Ph | c-Hex | 497 |
| 5 | 1 | 4-F—Ph | Et | 425 |
| 6 | 1 | 4-F—Ph | Me | 411 |
| 7 | 1 | 4-F—Ph | Ph—(CH$_2$)$_2$ | 501 |
| 8 | 1 | 4-F—Ph | Ph—CH=CH—CH$_2$ | 513 |
| 9 | 2 | 4-F—Ph—CH$_2$ | H | 425 |

TABLE 9B

| Compound Number | n | $R_1$ | $R_2$ | $R_3$ | Y | Mass Spectrum m/z [M + H]$^+$ |
|---|---|---|---|---|---|---|
| 10 | 0 | 4-F—Ph | H | H | CH=CH | 383 |
| 11 | 1 | 4-F—Ph | (1-Nap)—CH$_2$ | H | CH=CH | 537 |
| 12 | 1 | 4-F—Ph | (2-Cl—Ph)—CH$_2$ | H | CH=CH | 521 |
| 13 | 1 | 4-F—Ph | (2-Nap)—CH$_2$ | H | CH=CH | 537 |
| 14 | 1 | 4-F—Ph | (3-MeO—Ph)—CH$_2$ | H | CH=CH | 517 |
| 15 | 1 | 4-F—Ph | (3,4-di-MeO—Ph)—CH$_2$ | H | CH=CH | 547 |
| 16 | 1 | 4-F—Ph | (4-Cl—Ph)—CH$_2$ | H | CH=CH | 520 |
| 17 | 1 | 4-F—Ph | (4-F—Ph)—CH$_2$ | H | CH=CH | 505 |
| 18 | 1 | 4-F—Ph | (4-i-Pr—Ph)—CH$_2$ | H | CH=CH | 529 |
| 19 | 1 | 4-F—Ph | (4-Me—Ph)—CH$_2$ | H | CH=CH | 501 |
| 20 | 1 | 4-F—Ph | (4-MeO—Ph)—CH$_2$ | H | CH=CH | 517 |
| 21 | 1 | 4-F—Ph | (4-t-Bu—Ph)—CH$_2$ | H | CH=CH | 543 |
| 22 | 1 | 4-F—Ph | -6,7-Benzo- | | CH=CH | 445 |
| 23 | 1 | 4-F—Ph | c-Hex | H | CH=CH | 479 |
| 24 | 1 | 4-F—Ph | Et | H | CH=CH | 425 |
| 25 | 1 | 4-F—Ph | H | H | CH=CH | 397 |
| 26 | 1 | 4-Cl—Ph | H | H | CH=CH | 413 |
| 27 | 1 | 4-F—Ph | H | H | CH=CMe | 411 |
| 28 | 1 | 4-F—Ph | Me | H | CH=CH | 411 |
| 29 | 1 | 4-F—Ph | n-Pr | H | CH=CH | 439 |
| 30 | 1 | 4-F—Ph | Ph | H | CH=CH | 473 |
| 31 | 1 | 4-F—Ph | Ph—CH$_2$ | H | CH=CH | 487 |
| 32 | 1 | 4-F—Ph | Ph—(CH$_2$)$_2$ | H | CH=CH | 501 |
| 33 | 1 | 4-F—Ph | Ph—(CH$_2$)$_3$ | H | CH=CH | 515 |
| 34 | 1 | 4-F—Ph | Ph—CH=CH—CH$_2$ | H | CH=CH | 513 |
| 35 | 1 | 4-F—Ph | s-Bu | H | CH=CH | 453 |
| 36 | 2 | 4-F—Ph | -7,8-Benzo- | | CH=CH | 459 |
| 37 | 2 | 4-F—Ph | H | H | CH=CH | 411 |
| 38 | 2 | 4-F—Ph—CH$_2$ | H | H | CH=CH | 425 |

EXAMPLE 15

Ethyl (E)-3-[2-(4-fluorophenyl)-7-benzyl-4,5,6,7-tetrahydro-2H-indazol-3-yl]-2-propenoate (CP 196, RS step o)

Triethylphosphonoacetate (3.03 mmol, 0.706 g, 0.625 mL) in 2.5 mL of THF was added slowly under N$_2$ to a stirring suspension of oil-free NaH (3.09 mmol, 0.074 g) in 5 mL of THF. After 45 min, the solution was cooled added and the mixture was extracted with 100 mL of Et$_2$O. The organic phase was washed with brine, dried over Na$_2$SO$_4$, and concentrated to give 1.29 g of amber oil. The crude product was crystallized from Et$_2$O: hexanes to give 0.598 g (54%) of the title compound as an off-white solid, m.p. 117°-118° C.; $^1$H NMR (CDCl$_3$, 300 MHz) 1.30 (t, 3, J=7 Hz), 1.4-2.1 (complex, 4), 1.6-1.8 (complex, 3), 3.10 (m, 1), 3.54 (dd, 1, J=4, 13.5 Hz), 4.22 (q, 2, J=7 Hz), 6.20 (d, 1, J=16 Hz), 7.1-7.4 (complex, 9), 7.48 (d, 1, J=16 Hz); IR (KBr) 1705 cm$^{-1}$; MS (DCI) m/z 405 (base). Anal. Calcd. for C$_{25}$H$_{25}$FN$_2$O$_2$: C, 74.24; H, 6.23; N, 6.93. Found: C, 74.31; H, 6.09; N, 6.91.

General procedure for the preparation of 3-substituted 2-propenoates shown in Tables 10A and 10B (RS step o):

A solution of 11 mmol of triethylphosphonoacetate or triethyl phosphonopropionate in 10 mL of THF was added slowly under N$_2$ to a stirring suspension of 11.5 mmol of NaH in 15 mL of THF. After 45 min, the solution was cooled in an ice bath and the appropriately substituted aldehyde (10 mmol) from Table 3A, 3B, or 6 in THF (25 mL) was added dropwise. The mixture was allowed to warm to room temperature and was stirred overnight. Saturated aqueous NH$_4$Cl (100 mL) was added and the mixture was extracted with Et$_2$O. The organic phase was washed with brine, dried over Na$_2$SO$_4$, and concentrated. The crude product was crystallized or was carried on without purification.

TABLE 10A

| Compound Number | n | R$_1$ | R$_2$ | mp (°C.) | Mass Spectrum m/z [M + H]$^+$ |
|---|---|---|---|---|---|
| 197 | 0 | 4-F—Ph | H | 113-114 | 301 |
| 198 | 1 | 4-F—Ph | (4-F—Ph)—CH$_2$ | foam | 411 |
| 199 | 1 | 4-F—Ph | c-Hex | oil | 397 |
| 200 | 1 | 4-F—Ph | Et | 99-100 | 343 |
| 201 | 1 | 4-F—Ph | Me | oil | 329 |
| 202 | 1 | 4-F—Ph | Ph—CH=CH—CH$_2$ | foam | 431 |
| 203 | 2 | (4-F—Ph)—CH$_2$ | H | 75-76 | 343 |

TABLE 10B

| Compound Number | n | R$_1$ | R$_2$ | Y | mp (°C.) | Mass Spectrum m/z [M + H]$^+$ |
|---|---|---|---|---|---|---|
| 204 | 0 | 4-F—Ph | H | CH=CH | 94-95 | 301 |
| 205 | 1 | 4-F—Ph | (2-Cl—Ph)—CH$_2$ | CH=CH | oil | 439 |
| 206 | 1 | 4-F—Ph | (2-Et)Bu | CH=CH | oil | 399 |
| 207 | 1 | 4-F—Ph | (2-Nap)—CH$_2$ | CH=CH | 154-155 | 455 |
| 208 | 1 | 4-F—Ph | (3-MeO—Ph)—CH$_2$ | CH=CH | 135-137 | 435 |
| 209 | 1 | 4-F—Ph | (3,4-di-MeO—Ph)—CH$_2$ | CH=CH | foam | 465 |
| 210 | 1 | 4-F—Ph | (4-Cl—Ph)—CH$_2$ | CH=CH | oil | 439 |
| 211 | 1 | 4-F—Ph | (4-F—Ph)—CH$_2$ | CH=CH | oil | 411 |
| 212 | 1 | 4-F—Ph | (4-Me—Ph)—CH$_2$ | CH=CH | 135-136 | 419 |
| 213 | 1 | 4-F—Ph | (4-MeO—Ph)—CH$_2$ | CH=CH | oil | 435 |
| 214 | 1 | 4-F—Ph | (4-t-Bu—Ph)—CH$_2$ | CH=CH | oil | 461 |
| 215 | 1 | 4-F—Ph | c-Hex | CH=CH | oil | 419 |
| 216 | 1 | 4-F—Ph | Et | CH=CH | oil | 343 |
| 217 | 1 | 4-Cl—Ph | H | CH=CH | oil | 331 |
| 218 | 1 | 4-F—Ph | H | CH=CH | 76-77.5 | 315 |
| 219 | 1 | 4-F—Ph | H | CH=C(Me) | 134-135 | 329 |
| 220 | 1 | 4-F—Ph | Me | CH=CH | oil | 329 |
| 221 | 1 | 4-F—Ph | n-Pr | CH=CH | oil | 357 |
| 222 | 1 | 4-F—Ph | Ph—(CH$_2$)$_2$ | CH=CH | oil | 419 |
| 223 | 1 | 4-F—Ph | Ph—(CH$_2$)$_3$ | CH=CH | oil | 433 |
| 224 | 1 | 4-F—Ph | Ph—CH=CH—CH$_2$ | CH=CH | oil | 431 |
| 225 | 1 | 4-F—Ph | s-Bu | CH=CH | oil | 371 |
| 226 | 2 | 4-F—Ph | H | CH=CH | 53-55 | 329 |
| 227 | 2 | 4-F—Ph—CH$_2$ | H | CH=CH | oil | 343 |

EXAMPLE 16

(E)-3-[2-(4-Fluorophenyl)-7-benzyl-4,5,6,7-tetrahydro-2H-indazol-3-yl]2-propen-1-ol (CP 228, RS step p):

A 1.5M solution of (i-Bu)$_2$AlH in toluene (6.53 mmol, 4.35 mL) was added under N$_2$ to an ice cold solution of 1.10 g (6.53 mmol) of Compound 196 in 11 mL of THF. The solution was stirred for 1.5 h and was quenched with 0.5 mL of MeOH. When the initial bubbling had ceased, 35 mL of 1N aqueous HCl was added and the mixture was extracted with 150 mL of ether. The organic phase was washed sequentially with water, saturated aqueous NaHCO₃, and brine. After drying over Na₂SO₄, the solvent was evaporated to give 0.89 g of an off-white solid. Recrystallization from EtOAc:hexanes afforded 0.62 g (63%) of the title compound as a white solid, m.p. 185°–186° C.; $^1$H NMR (CDCl₃, 300 MHz) 1.4–2.0 (complex, 5), 2.62 (m, 3), 3.05 (m, 1), 3.54 (dd, 1, J=4, 13.5 Hz), 4.27 (t, 2, J=5 Hz), 6.16 (dt, 1, J=16, 5.5 Hz), 6.43 (d, 1, J=16 Hz), 7.1–7.5 (complex, 9); IR (KBr) 3300, 1515 cm$^{-1}$; MS (DCI) m/z 363 (base), 345. Anal. Calcd. for C₂₃H₂₃FN₂O: C, 76.22; H, 6.40; N, 7.73. Found: C, 75.73; H, 6.01; N, 7.91.

General procedure for the preparation of 3-substituted 2-propen-1-ols shown in Tables 11A and 11B (RS step p):

A 1.5M solution of (i-Bu)₂AlH in toluene (24 mmol) was added under N₂ to an ice cold solution of 10 mmol of the appropriately substituted ester from Table 10A or 10B in 50 mL of THF. The solution was stirred for 1.5 h and was quenched with 2 mL of MeOH. When the initial bubbling had ceased, 100 mL of 1N aqueous HCl was added and the mixture was extracted with 300 mL of ether. The organic phase was washed sequentially with water, saturated aqueous NaHCO₃, and brine. After drying over Na₂SO₄, the solvent was evaporated and the crude product was purified by recrystallization or MPLC.

TABLE 11A

| Compound Number | n | R₁ | R₂ | mp (°C.) | Mass Spectrum m/z [M + H]⁺ |
|---|---|---|---|---|---|
| 229 | 0 | 4-F—Ph | H | 135–136 | 259 |
| 230 | 1 | 4-F—Ph | (4-F—Ph)—CH₂ | 171–173 | 381 |
| 231 | 1 | 4-F—Ph | c-Hex | oil | 355 |
| 232 | 1 | 4-F—Ph | Et | yellow foam | 301 |
| 233 | 1 | 4-F—Ph | Me | 115–116 | 287 |
| 234 | 1 | 4-F—Ph | Ph—CH=CH—CH₂ | oil | 389 |
| 235 | 2 | (4-F—Ph)—CH₂ | H | oil | 301 |

TABLE 11B

| Compound Number | n | R₁ | R₂ | Y | mp (°C.) | Mass Spectrum m/z [M + H]⁺ |
|---|---|---|---|---|---|---|
| 236 | 0 | 4-F—Ph | H | CH=CH | 144–145 | 259 |
| 237 | 1 | 4-F—Ph | (2-Cl—Ph)—CH₂ | CH=CH | 177–178 | 397 |
| 238 | 1 | 4-F—Ph | (2-Et)Bu | CH=CH | oil | 357 |
| 239 | 1 | 4-F—Ph | (2-Nap)—CH₂ | CH=CH | 205–207 | 413 |
| 240 | 1 | 4-F—Ph | (3-MeO—Ph)—CH₂ | CH=CH | foam | 393 |
| 241 | 1 | 4-F—Ph | (3,4-di-MeO—Ph)—CH₂ | CH=CH | 183–184 | 423 |
| 242 | 1 | 4-F—Ph | (4-Cl—Ph)—CH₂ | CH=CH | 204–206 | 397 |
| 243 | 1 | 4-F—Ph | (4-F—Ph)—CH₂ | CH=CH | 183–185 | 381 |
| 244 | 1 | 4-F—Ph | (4-Me—Ph)—CH₂ | CH=CH | 184–186 | 377 |
| 245 | 1 | 4-F—Ph | (4-MeO—Ph)—CH₂ | CH=CH | 172–173 | 393 |
| 246 | 1 | 4-F—Ph | (4-t-Bu—Ph)—CH₂ | CH=CH | 141–142 | 419 |
| 247 | 1 | 4-F—Ph | c-Hex | CH=CH | oil | 355 |
| 248 | 1 | 4-F—Ph | Et | CH=CH | 140–142 | 301 |
| 249 | 1 | 4-Cl—Ph | H | CH=CH | 171–173 | 289 |
| 250 | 1 | 4-F—Ph | H | CH=CH | 145–146 | 273 |
| 251 | 1 | 4-F—Ph | H | CH=C(Me) | 149–150 | 287 |
| 252 | 1 | 4-F—Ph | Me | CH=CH | 139–140 | 287 |
| 253 | 1 | 4-F—Ph | n-Pr | CH=CH | 140–141 | 315 |
| 254 | 1 | 4-F—Ph | Ph—(CH₂)₂ | CH=CH | 116–118 | 377 |
| 255 | 1 | 4-F—Ph | Ph—(CH₂)₃ | CH=CH | 105–108 | 391 |
| 256 | 1 | 4-F—Ph | Ph—CH=CH—CH₂ | CH=CH | oil | 389 |
| 257 | 1 | 4-F—Ph | s-Bu | CH=CH | oil | 329 |
| 258 | 2 | 4-F—Ph | H | CH=CH | 104–105 | 287 |
| 259 | 2 | (4-F—Ph)—CH₂ | H | CH=CH | 78–79 | 301 |

EXAMPLE 17

(E)-3-[2-(4-Fluorophenyl)-2,4,5,6-tetrahydrobenzo[6,7-]cyclohepta-[1,2-c]pyrazol-3-yl]-2-propen-1-ol (CP 260, RS step q)

1-Benzosuberone (25 mmol, 4.10 g, 3.74 mL) was added dropwise under N₂ to a stirring suspension of 4.23 g (26 mmol) of 4-fluorophenylhydrazine•HCl and 2.13 g (26 mmol) of NaOAc in 15 mL of absolute EtOH. The mixture was refluxed for 3 h and allowed to stir at room temperature overnight. After concentration, the residue was partitioned between water and Et$_2$O. The organic phase was washed with saturated aqueous NaHCO$_3$ and brine, dried over Na$_2$SO$_4$, and concentrated to give 6.68 g of crude hydrazone as an orange solid. The crude product was dissolved in 25 mL of THF and added dropwise under N$_2$ to a solution of LDA (made by adding 7.34 mL (52.3 mmol, 5.29 g) of diisopropylamine in 20 mL of THF to 33.7 mL (52.3 mmol) of 1.6M n-BuLi in hexanes) at −10° C. The resulting dark brown solution was stirred for 30 min and was treated with a solution of methyl 4-tetrahydropyranyloxy-2-butenoate (Harnish, W.; Morera, E.; Ortar, G. *J. Org. Chem.*, 1985, 50, 1990-2) in 5 mL of THF. After 1.5 h, 42 mL of 3N aqueous HCl was added to the cold solution, which was then refluxed for 15 min. Et$_2$O (150 mL) was added and the organic layer was washed with saturated aqueous NaHCO$_3$ and brine. After drying over Na$_2$SO$_4$, the mixture was concentrated to give 12 g of light brown oil. The crude residue was refluxed under N$_2$ for 8 h with 0.31 g (1.25 mmol) of pyrdinium p-toluenesulfonate in 50 mL of MeOH. The solution was concentrated and the residue was partitioned between Et$_2$O and water. The organic phase was washed with saturated aqueous NaHCO$_3$ and brine, dried over Na$_2$SO$_4$, and concentrated to give 9.2 g of brown oil. Purification by MPLC using 1:3 EtOAc:hexanes afforded 3.35 g of yellow solid which was recrystallized from EtOAc:hexanes to give 3.00 g (36%) of the title compound as a white solid, m.p. 127°-128° C.; $^1$H NMR (CDCl$_3$, 300 MHz) 2.15 (m, 2), 2.84 (m, 4), 4.30 (m, 2), 6.16 (dt, 1, J=16, 5 Hz), 6.44 (d, 1, J=16 Hz), 7.2 (complex, 5), 7.50 (m, 2), 8.07 (m, 1); IR (KBr) 3300 (broad), 1515, 1223 cm$^{-1}$; MS (DCI) m/z 335 (base), 317. Anal. Calcd. for C$_{21}$H$_{19}$FN$_2$O: C, 75.43; H, 5.73; N, 8.38. Found: C, 75.26; H, 5.52; N, 8.24.

EXAMPLE 18

(E)-3-[4,5-Dihydro-2-(4-fluorophenyl)-2H-benz[g]indazol-3-yl]-2-propen-1-ol (CP 261, RS step q)

α-Tetralone (25 mmol, 3.65 g, 3.33 mL) was added dropwise under N$_2$ to a stirring suspension of 4.23 g (26 mmol) of 4-fluorophenylhydrazine•HCl and 2.13 g (26 mmol) of NaOAc in 15 mL of absolute EtOH. The mixture was refluxed for 2 h, cooled, and concentrated to remove the solvent. The residue was partitioned between water and Et$_2$O. The organic phase was washed with saturated aqueous NaHCO$_3$ and brine, dried over Na$_2$SO$_4$, and concentrated to give 6.21 g of crude hydrazone as a yellow solid. The crude product was dissolved in 30 mL of THF and added dropwise under N$_2$ to a solution of LDA (made by adding 7.18 mL (51.2 mmol, 5.18 g) of diisopropylamine in 10 mL of THF to 33.0 mL (51.2 mmol) of 1.55M n-BuLi in hexanes) at −10° C. The resulting dark brown solution was stirred for 30 min and was treated with a solution of methyl 4-tetrahydropyranyloxy-2-butenoate (Harnish, W.; Morera, E.; Ortar, G. *J. Org. Chem.*, 1985, 50, 1990-2) in 15 mL of THF. After 1.5 h, 42 mL of 3N aqueous HCl was added to the cold solution, which was then refluxed for 1 h. Et$_2$O (150 mL) was added and the organic layer was washed with saturated aqueous NaHCO$_3$ and brine. After drying over Na$_2$SO$_4$, the mixture was concentrated to give 10.2 g of a light brown oil. The crude residue was refluxed under N$_2$ for 8 h with 0.31 g (1.25 mmol) of pyrdinium p-toluenesulfonate in 50 mL of MeOH. The solution was concentrated and the residue was partitioned between Et$_2$O and water. The organic phase was washed with saturated aqueous NaHCO$_3$ and brine, dried over Na$_2$SO$_4$, and concentrated to give 8.44 g of a brown oil. Purification by MPLC using 1:3 EtOAc:hexanes afforded 3.03 g of an off-white solid which was recrystallized from EtOAc:hexanes to give 2.37 g (37%) of the title compound as an off-white solid, m.p. 149°-150° C.; $^1$H NMR (CDCl$_3$, 300 MHz) 1.70 (t, 1, J=6 Hz), 2.91 (m, 2), 3.02 (m, 2), 4.31 (dt, 2, J=1.5, 4.5 Hz), 6.21 (dt, 1, J=16, 5 Hz), 6.46 (dd, 1, J=1.5, 16 Hz), 7.18 (t, 2, J=8.5 Hz), 7.25 (m, 3), 7.48 (dd, 2, J=5, 8.5 Hz), 7.92 (m, 1); IR (KBr) 3300 (broad), 1509, 1221 cm$^{-1}$; MS (DCI) m/z 321 (base), 303. Anal. Calcd. for C$_{20}$H$_{17}$FN$_2$O: C, 74.98; H, 5.35; N, 8.74. Found: C, 74.78; H, 5.33; N, 8.97.

EXAMPLE 19

(E)-3-[2-(4-Fluorophenyl)-7-benzyl-4,5,6,7-tetrahydro-2H-indazol-3-yl]-2-propenal (CP 262, RS step r)

MnO$_2$ (30 mmol, 2.20 g) was added in one portion to a stirring suspension of 0.84 g (2.32 mmol) of Compound 228 in 15 mL of benzene. The mixture was refluxed gently under N$_2$ for 3 h. After cooling, the slurry was filtered through a Celite pad and the solids were washed with 100 mL of CH$_2$Cl$_2$. The filtrate was concentrated to give 0.75 g of a yellow solid which was purified by MPLC (1:8 EtOAc:hexanes) to provide 0.529 g (63%) of the title compound as a pale yellow solid, m.p. 130°-131° C.; $^1$H NMR (CDCl$_3$, 300 MHz) 1.6-2.1 (complex, 4), 2.6-2.8 (complex, 3), 3.10 (m, 1), 3.54 (dd, 1, J=4, 13.5 Hz), 6.48 (dd, 1, J=7.5, 16 Hz), 7.1-7.5 (complex, 10), 9.52 (d, 1, J=7.5 Hz); IR (KBr) 1677, 1617, 1512 cm$^{-1}$; MS (DCI) m/z 361 (base), 307, 269, 241, 178. Anal. Calcd. for C$_{23}$H$_{21}$FN$_2$O: C, 76.65; H, 5.87; N, 7.77. Found: C, 76.47; H, 5.61; N, 7.35.

General procedure for the preparation of 3-substituted 2-propenals shown in Tables 12A and 12B. RS step r:

Method A: MnO$_2$ (100–120 mmol) was added in one portion to a stirring suspension of 10 mmol of the appropriately substituted alcohol from Table 11A or 11B or Example 17 or 18 in benzene (60 mL). The mixture was refluxed gently under N$_2$ until TLC analysis indicated that the starting material was completely consumed. After cooling, the slurry was filtered through a Celite pad and the black solids were washed with 250 mL of CH$_2$Cl$_2$. The filtrate was concentrated and the crude product was purified by MPLC or recrystallization.

Method B: CrO$_3$ (60 mmol) was added under N$_2$ in several portions to an ice-cold solution of 120 mmol of pyridine in 100 mL of CH$_2$Cl$_2$. The mixture was stirred at room temperature for 15 min and was re-cooled to 0° C. The appropriately substituted alcohol from Table 11A or 11B was either dissolved in a minimum amount of CH$_2$Cl$_2$ and added dropwise or, if solid, was added in 5-10 portions over a 30 min period. The slurry was stirred 30-45 min at 0° C. and was allowed to stir at room temperature until TLC analysis indicated the reaction was complete. Et$_2$O (200 mL) was added and the solvent was decanted from the tarry residue through a Celite pad. The residue was sonicated with two 100 mL portions of Et$_2$O, which were also decanted through Celite. The combined filtrates were washed successively with 100 mL of 1N aqueous HCl, 100 mL of water, two 100 mL portions of saturated aqueous NaHCO$_3$, and brine. The ethereal solution was dried (Na$_2$SO$_4$), concentrated, and purified by MPLC or recrystallization.

TABLE 12A

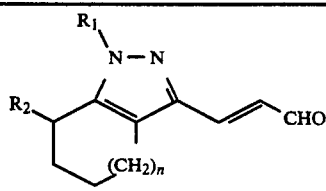

| Compound Number | Method | n | R$_1$ | R$_2$ | mp (°C.) | Mass Spectrum m/z [M + H]$^+$ |
|---|---|---|---|---|---|---|
| 263 | B | 0 | 4-F—Ph | H | 138-139 | 257 |
| 264 | A | 1 | 4-F—Ph | (4-F—Ph)—CH$_2$ | 133-136 | 379 |
| 265 | A | 1 | 4-F—Ph | c-Hex | foam | 353 |
| 266 | A | 1 | 4-F—Ph | Et | 118-121 | 299 |
| 267 | A | 1 | 4-F—Ph | Me | oil | 285 |
| 268 | A | 1 | 4-F—Ph | Ph—CH=CH—CH$_2$ | foam | 387 |
| 269 | A | 2 | (4-F—Ph)—CH$_2$ | H | oil | 299 |

TABLE 12B

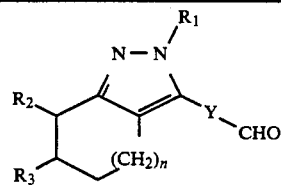

| Compound Number | Method | n | R$_1$ | R$_2$ | R$_3$ | Y | mp (°C.) | Mass Spectrum m/z [M + H]$^+$ |
|---|---|---|---|---|---|---|---|---|
| 270 | B | 0 | 4-F—Ph | H | H | CH=CH | 127-128 | 257 |
| 271 | A | 1 | 4-F—Ph | (2-Cl—Ph)—CH$_2$ | H | CH=CH | 184-185 | 395 |
| 272 | A | 1 | 4-F—Ph | (2-Et)Bu | H | CH=CH | 98-100 | 355 |
| 273 | A | 1 | 4-F—Ph | (2-Nap)—CH$_2$ | H | CH=CH | 174-175 | 411 |
| 274 | A | 1 | 4-F—Ph | (3-MeO—Ph)—CH$_2$ | H | CH=CH | 97-99 | 391 |
| 275 | A | 1 | 4-F—Ph | (3,4-di-MeO—Ph)—CH$_2$ | H | CH=CH | foam | 421 |
| 276 | A | 1 | 4-F—Ph | (4-Cl—Ph)—CH$_2$ | H | CH=CH | 144-145 | 395 |
| 277 | A | 1 | 4-F—Ph | (4-F—Ph)—CH$_2$ | H | CH=CH | oil | 379 |
| 278 | A | 1 | 4-F—Ph | (4-Me—Ph)—CH$_2$ | H | CH=CH | 160-162 | 375 |
| 279 | A | 1 | 4-F—Ph | (4-MeO—Ph)—CH$_2$ | H | CH=CH | 141-142 | 391 |
| 280 | A | 1 | 4-F—Ph | (4-t-Bu—Ph)—CH$_2$ | H | CH=CH | 145-148 | 417 |
| 281 | A | 1 | 4-F—Ph | -6,7-Benzo- | | CH=CH | foam | 319 |
| 282 | A | 1 | 4-F—Ph | c-Hex | H | CH=CH | oil | 353 |
| 283 | A | 1 | 4-F—Ph | Et | H | CH=CH | 99-101 | 299 |
| 284 | B | 1 | 4-Cl—Ph | H | H | CH=CH | 133-134 | 287 |
| 285 | B | 1 | 4-F—Ph | H | H | CH=CH | 122-123 | 271 |
| 286 | A | 1 | 4-F—Ph | H | H | CH=C(Me) | 172-173 | 285 |
| 287 | A | 1 | 4-F—Ph | Me | H | CH=CH | 145-146 | 285 |
| 288 | A | 1 | 4-F—Ph | n-Pr | H | CH=CH | 92-93 | 313 |
| 289 | A | 1 | 4-F—Ph | Ph—(CH$_2$)$_2$ | H | CH=CH | 132-134 | 375 |
| 290 | A | 1 | 4-F—Ph | Ph—(CH$_2$)$_3$ | H | CH=CH | oil | 389 |
| 291 | A | 1 | 4-F—Ph | Ph—CH=CH—CH$_2$ | H | CH=CH | foam | 387 |
| 292 | A | 1 | 4-F—Ph | s-Bu | H | CH=CH | oil | 327 |
| 293 | A | 2 | 4-F—Ph | -7,8-Benzo- | | CH=CH | 208-210 | 333 |
| 294 | A | 2 | 4-F—Ph | H | H | CH=CH | 92-93 | 285 |
| 295 | A | 2 | (4-F—Ph)—CH$_2$ | H | H | CH=CH | oil | 299 |

EXAMPLE 20

Ethyl (E)-(3RS,5SR)-7-[7-benzyl-2-(4-fluorophenyl)-4,5,6,7-tetrahydro-2H-indazol-3-yl]-3,5-dihydroxy-6-heptenoate (CP 47, RS step s)

A solution of 1.11 mL of ethyl acetoacetate (8.72 mmol, 1.13 g) in 10 mL of THF was added dropwise under N$_2$ to a stirring suspension of 0.220 g (9.16 mmol) of oil-free NaH in 10 mL of THF. The mixture was stirred for 30 min and cooled to −10° C. in an ice/acetone bath. n-BuLi in hexanes (1.6M, 8.72 mmol, 5.45 mL) was added slowly, producing a pale yellow solution. After 30 min, a solution of 2.86 g (7.93 mmol) of Compound 262 in 25 mL of THF was added and the resulting yellow solution was stirred for 45 min. Saturated aqueous NH$_4$Cl (50 mL) was added and the mixture was extracted with 100 mL of Et$_2$O. The organic solution was washed with brine, dried over Na$_2$SO$_4$, and concentrated to give 3.84 g of crude hydroxy keto ester as an orange oil.

The crude intermediate was dissolved in 8 mL of MeOH and 25 mL of THF. A 1.0M solution of Et$_3$B in THF (8.60 mmol, 8.60 mL) was added and 20 mL of air was bubbled into the solution via syringe. The solution was stirred under $N_2$ for 2 h and was cooled to $-78°$ C. $NaBH_4$ (8.60 mmol, 0.33 g) was added in one portion. The mixture was allowed to warm slowly to room temperature and was stirred overnight. Saturated aqueous $NH_4Cl$ (100 mL) was added and the mixture was extracted with 150 mL of $Et_2O$. The organic solution was washed with brine, dried over $Na_2SO_4$, and concentrated to give an oil which was dissolved in 50 mL of MeOH and stirred vigorously under air overnight. The solution was concentrated to give 3.86 g of a yellow oil. Purification by MPLC using 2:3 EtOAc:hexanes yielded 1.83 g (47%) of the title compound as a white foam; $^1$H NMR (CDCl$_3$, 300 MHz) 1.27 (t, 3, J=7 Hz), 1.3-2.0 (complex, 6), 2.48 (d, 2, J=6 Hz), 2.60 (m, 3), 3.03 (m, 1), 3.55 (m, 1), 3.63 (s, 1), 3.78 (s, 1), 4.17 (q, 2, J=7 Hz), 4.30 (m, 1), 4.50 (m, 1), 6.00 (dd, 1, J=6, 16 Hz), 6.44 (d, 1, J=16 Hz), 7.1-7.5 (complex, 9); $^{13}$C NMR (CDCl$_3$, 75 MHz) 14.2, 21.6, 22.8, 27.8, 36.2, 40.7, 41.5, 42.7, 60.9, 68.4, 72.5, 115.7, 116.0 ($J_{C-F}$=23 Hz), 117.9, 125.9, 127.3 ($J_{C-F}$=8 Hz), 128.2, 129.3, 135.0, 135.4, 136.2, 140.6, 153.3, 161.8 ($J_{C-F}$=247 Hz), 172.5; IR (KBr) 3400 (broad), 1732, 1514 cm$^{-1}$; MS (DCI) m/z 493, 457, 401, 333, 241, 91 (base). Anal. Calcd. for $C_{29}H_{33}FN_2O_4$: C, 70.71; H, 6.75; N, 5.69. Found: C, 70.90; H, 7.04; N, 5.67.

General procedure for the preparation of 7-substituted (E)-(3RS,5SR)-3,5-dihydroxy-6-heptenoates shown in Tables 13A and 13B (RS step s):

A solution of 11 mmol of ethyl acetoacetate in 10 mL of THF was added dropwise under $N_2$ to a stirring suspension of 11.5 mmol of oil-free NaH in 15 mL of THF. The mixture was stirred for 30 min and cooled to $-10°$ C. in an ice/acetone bath. n-BuLi in hexanes (11 mmol of a 1.6M solution) was added slowly, producing a pale yellow solution. After 30 min, a solution of 10 mmol of the appropriately substituted aldehyde from Table 12A or 12B in 30 mL of THF was added and the resulting yellow solution was stirred for about 1 h. Saturated aqueous $NH_4Cl$ (75 mL) was added and the mixture was extracted with 150 mL of $Et_2O$. The organic solution was washed with brine, dried over $Na_2SO_4$, and concentrated to give the crude hydroxy keto ester which was carried on without purification.

The crude intermediate was dissolved in 10 mL of MeOH and 30 mL of THF. A 1.0M solution of $Et_3B$ in THF (11 mmol) was added and 20 mL of air was bubbled into the solution via syringe. The solution was stirred under $N_2$ for 2 h and was cooled to $-78°$ C. $NaBH_4$ (11 mmol) was added in one portion, causing some gas evolution. The mixture was allowed to warm slowly to room temperature and was stirred overnight. Saturated aqueous $NH_4Cl$ (150 mL) was added and the mixture was extracted with 200 mL of $Et_2O$. The organic solution was washed with brine, dried over $Na_2SO_4$, and concentrated. The residue, which smelled of excess $Et_3B$, was then dissolved in MeOH and stirred vigorously under air until TLC analysis showed complete conversion of the boron intermediates to the desired product (4-24 h). The MeOH was removed by rotary evaporation and the crude material was purified by MPLC.

TABLE 13A

| Compound | n | $R_1$ | $R_2$ | Mass Spectrum m/z $[M + H]^+$ |
|---|---|---|---|---|
| 48 | 0 | 4-F—Ph | H | 389 |
| 49 | 1 | 4-F—Ph | (4-F—Ph)—CH$_2$ | 511 |
| 50 | 1 | 4-F—Ph | c-Hex | 485 |
| 51 | 1 | 4-F—Ph | Et | 431 |
| 52 | 1 | 4-F—Ph | Me | 417 |
| 53 | 1 | 4-F—Ph | Ph—CH=CH—CH$_2$ | 515 |
| 54 | 2 | (4-F—Ph)—CH$_2$ | H | 431 |

TABLE 13B

| Compound Number | n | $R_1$ | $R_2$ | $R_3$ | Y | Mass Spectrum m/z $[M + H]^+$ |
|---|---|---|---|---|---|---|
| 55 | 0 | 4-F—Ph | H | H | CH=CH | 389 |
| 56 | 1 | 4-F—Ph | (2-Cl—Ph)—CH$_2$ | H | CH=CH | 528 |
| 57 | 1 | 4-F—Ph | (2-Et)Bu | H | CH=CH | 487 |
| 58 | 1 | 4-F—Ph | (3-MeO—Ph)—CH$_2$ | H | CH=CH | 523 |
| 59 | 1 | 4-F—Ph | (3,4-di-MeO—Ph)—CH$_2$ | H | CH=CH | 553 |
| 60 | 1 | 4-F—Ph | (4-Cl—Ph)—CH$_2$ | H | CH=CH | 528 |
| 61 | 1 | 4-F—Ph | (4-F—Ph)—CH$_2$ | H | CH=CH | 511 |
| 62 | 1 | 4-F—Ph | (4-Me—Ph)—CH$_2$ | H | CH=CH | 507 |
| 63 | 1 | 4-F—Ph | (4-MeO—Ph)—CH$_2$ | H | CH=CH | 523 |

TABLE 13B-continued

![structure]

| Compound Number | n | R₁ | R₂ | R₃ | Y | Mass Spectrum m/z [M + H]⁺ |
|---|---|---|---|---|---|---|
| 64 | 1 | 4-F—Ph | (4-t-Bu—Ph)—CH₂ | H | CH=CH | 549 |
| 65 | 1 | 4-F—Ph | -6,7-Benzo- |  | CH=CH | 451 |
| 66 | 1 | 4-F—Ph | c-Hex | H | CH=CH | 485 |
| 67 | 1 | 4-F—Ph | Et | H | CH=CH | 431 |
| 68 | 1 | 4-Cl—Ph | H | H | CH=CH | 419 |
| 69 | 1 | 4-F—Ph | H | H | CH=CH | 403 |
| 70 | 1 | 4-F—Ph | H | H | CH=CMe | 417 |
| 71 | 1 | 4-F—Ph | Me | H | CH=CH | 417 |
| 72 | 1 | 4-F—Ph | n-Pr | H | CH=CH | 445 |
| 73 | 1 | 4-F—Ph | Ph—(CH₂)₂ | H | CH=CH | 507 |
| 74 | 1 | 4-F—Ph | Ph—(CH₂)₃ | H | CH=CH | 521 |
| 75 | 1 | 4-F—Ph | s-Bu | H | CH=CH | 459 |
| 76 | 2 | 4-F—Ph | -7,8-Benzo- |  | CH=CH | 465 |
| 77 | 2 | 4-F—Ph | H | H | CH=CH | 417 |
| 78 | 2 | (4-F—Ph)—CH₂ | H | H | CH=CH | 431 |

EXAMPLE 21

(E)-(4RS,6SR)-6-[2-[7-Benzyl-2-(4-fluorophenyl)-4,5,6,7-tetrahydro-2H-indazol-3-yl]ethenyl]-4-hydroxy-3,4,5,6-tetrahydro-2H-pyran-2-one (CP 79, RS step w)

A 5.0 mL (1.25 mmol) portion of 0.25N aqueous NaOH was added slowly to an ice-cold solution of 0.500 g (1.02 mmol) of Compound 47 in 15 mL of methanol. After 15 min, the solution was allowed to warm to room temperature and was stirred for 1 h. The solution was concentrated to dryness using a rotary evaporator and was mixed with 50 mL of water and 100 mL of CH₂Cl₂. The mixture was acidified to pH 2-3 with aqueous 1N HCl. The aqueous layer was extracted with 50 mL of CH₂Cl₂ and the combined organic layers were washed with brine, dried over Na₂SO₄, and concentrated. The crude dihydroxy acid (0.49 g) was dissolved in 12 mL of CH₂Cl₂ and cooled in an ice bath. 1-Cyclohexyl-3-(2-morpholinoethyl)carbodiimide metho-p-toluenesulfonate (1.07 mmol, 0.455 g) was added in one portion and the mixture was allowed to warm slowly to room temperature and was stirred overnight. EtOAc (100 mL) was added and the white solids were removed by suction filtration. The solids were washed with more EtOAc and the combined filtrates were washed with water and brine and dried (Na₂SO₄). The solution was concentrated to give 0.60 g of crude product which was purified by MPLC (1:1 EtOAc:hexanes) to provide 0.29 g (64%) of the title compound as a white solid, m.p. 185°-187° C.; ¹H NMR (CDCl₃, 300 MHz) 1.4–2.1 (complex, 6), 2.21 (d, 1, J=2.5 Hz), 2.62 (m, 4), 2.74 (dd, 1, J=4.5, 18 Hz), 3.06 (m, 1), 3.53 (dt, 1, J=13.5, 3.5), 4.40 (m, 1), 5.25 (m, 1), 6.01 (dd, 1, J=6.5, 16 Hz), 6.49 (d, 1, J=16 Hz), 7.1–7.5 (complex, 9); IR (KBr) 3300 (broad), 1741, 1513 cm⁻¹; MS (DCI) m/z 447, 429, 385 (base), 359. Anal. Calcd. for C₂₇H₂₇FN₂O₃: C, 72.63; H, 6.09; N, 6.27. Found: C, 72.61; H, 6.10; N, 5.97.

General procedure for the preparation of 6-substituted (E)-(4RS,6SR)-4-hydroxy-3,4,5,6-tetrahydro-2H-pyran-2-ones shown in Table 14, RS step w A 5.0 mL (1.25 mmol) portion of 0.25N aqueous NaOH was added slowly to an ice-cold solution of 1.02 mmol of the appropriately substituted ester from Table 8, 13A, or 13B in methanol (15 mL). After 15 min, the solution was allowed to warm to room temperature and was stirred for 1 h. The solution was concentrated to dryness using a rotary evaporator and was mixed with 50 mL of water and 100 mL of CH₂Cl₂. The mixture was acidified to pH 2-3 with aqueous 1N HCl. The aqueous layer was extracted with 50 mL of CH₂Cl₂ and the combined organic layers were washed with brine, dried over Na₂SO₄, and concentrated. The crude dihydroxy acid was dissolved in 12 mL of CH₂Cl₂ and cooled in an ice bath. 1-Cyclohexyl-3-(2-morpholinoethyl)carbodiimide metho-p-toluenesulfonate (1.1 mmol) was added in one portion and the mixture was allowed to warm slowly to room temperature and was stirred overnight. EtOAc (100 mL) was added and the white solids were removed by suction filtration. The solids were washed with more EtOAc and the combined filtrates were washed with water and brine and dried (Na₂SO₄). The solution was concentrated and the crude product was purified by MPLC.

TABLE 14

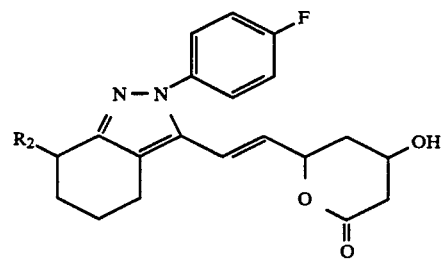

| Compound Number | R₂ | mp (°C.) | Mass Spectrum m/z [M + H]⁺ |
|---|---|---|---|
| 80 | (2-Et)Bu | foam | 441 |
| 81 | (2-Nap)—CH₂ | foam | 497 |
| 82 | (4-t-Bu—Ph)—CH₂ | foam | 503 |
| 83 | H | foam | 357 |

We claim:

1. A compound of the formula X:

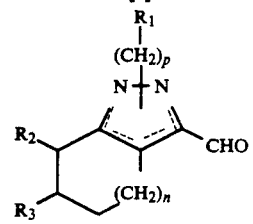

wherein $R_1$ is selected from any one of H, alkyl, aryl, or substituted aryl; wherein $R_2$ is selected from any one of alkyl, aryl, substituted aryl, aralkyl, substituted aralkyl, aralkenyl, or cycloalkyl;

wherein $R_3$ is H; or wherein $R_2$ and $R_3$ may be taken together to form a benzo or naphtho ring system;

wherein n=0 to 3 and p=0 to 3 and pharmaceutically acceptable acid salts thereof.

* * * * *